United States Patent
Longo et al.

(10) Patent No.: US 10,898,356 B2
(45) Date of Patent: Jan. 26, 2021

(54) DELIVERY DEVICE AND METHOD OF DELIVERY

(71) Applicant: Intact Vascular, Inc., Wayne, PA (US)

(72) Inventors: Michael Longo, Glenmoore, PA (US); Douglas Evans, Downingtown, PA (US); William James Harrison, Signal Mountain, TN (US)

(73) Assignee: Intact Vascular, Inc., Wayne, PA (US)

( * ) Notice: Subject to any disclaimer, the term of this patent is extended or adjusted under 35 U.S.C. 154(b) by 157 days.

(21) Appl. No.: 15/194,410

(22) Filed: Jun. 27, 2016

(65) Prior Publication Data

US 2016/0374839 A1 Dec. 29, 2016

Related U.S. Application Data

(63) Continuation of application No. 14/935,154, filed on Nov. 6, 2015, now Pat. No. 9,445,929, which is a (Continued)

(51) Int. Cl.
*A61F 2/915* (2013.01)
*A61F 2/966* (2013.01)
(Continued)

(52) U.S. Cl.
CPC ............. *A61F 2/915* (2013.01); *A61F 2/844* (2013.01); *A61F 2/86* (2013.01); *A61F 2/962* (2013.01);
(Continued)

(58) Field of Classification Search
CPC .......... A61F 2/915; A61F 2/844; A61F 2/962; A61F 2/86; A61F 2/966
See application file for complete search history.

(56) References Cited

U.S. PATENT DOCUMENTS 3,051,172 A 8/1962 Bruchhaus
3,221,746 A 12/1965 Noble
(Continued)

FOREIGN PATENT DOCUMENTS

AU 2008335140 11/2012
AU 2011274392 11/2013
(Continued)

OTHER PUBLICATIONS

International Search Report and Written Opinion, re PCT Application No. PCT/US2016/014161, dated Apr. 12, 2016.
(Continued)

*Primary Examiner* — Richard G Louis
(74) *Attorney, Agent, or Firm* — Knobbe Martens Olson & Bear, LLP

(57) ABSTRACT

A delivery device can provide sequential delivery of a plurality of intraluminal devices or tacks held in a compressed state on the delivery device. Delivery platforms on the delivery device can hold a tack in a compressed position and have a unique shape, such as a non-constant outer diameter, an hourglass shape, a tapered proximal half, ridges, dimples, etc. This unique shape can be positioned between annular pusher bands that may also be radiopaque markers. In some embodiments, the unique shape is provided by a sleeve of flexible material with the unique shape surrounding a harder inner shaft. Further, the annular pusher bands can be made of wire or sections of material to increase flexibility while remaining radiopacity. A tack deployment method can include alignment of radiopaque markers on the outer sheath and the tack to be deployed prior to deployment.

27 Claims, 6 Drawing Sheets

Related U.S. Application Data continuation of application No. 14/656,462, filed on Mar. 12, 2015, now Pat. No. 9,375,336.

(60) Provisional application No. 62/109,534, filed on Jan. 29, 2015.

(51) Int. Cl.
   *A61F 2/86* (2013.01)
   *A61F 2/962* (2013.01)
   *A61F 2/844* (2013.01)
   *A61F 2/82* (2013.01)
   *A61F 2/95* (2013.01)

(52) U.S. Cl.
   CPC ............ *A61F 2/966* (2013.01); *A61F 2/9517* (2020.05); *A61F 2002/826* (2013.01); *A61F 2002/91575* (2013.01); *A61F 2002/91583* (2013.01); *A61F 2002/9665* (2013.01); *A61F 2250/0019* (2013.01); *A61F 2250/0039* (2013.01); *A61F 2250/0098* (2013.01)

(56) References Cited

U.S. PATENT DOCUMENTS

| | | |
|---|---|---|
| 3,635,223 A | 1/1972 | Klieman |
| 4,292,974 A | 10/1981 | Fogarty et al. |
| 4,446,867 A | 5/1984 | Leveen et al. |
| 4,465,072 A | 8/1984 | Taheri |
| 4,515,587 A | 5/1985 | Schiff |
| 4,545,367 A | 10/1985 | Tucci |
| 4,545,390 A | 10/1985 | Leary |
| 4,552,127 A | 11/1985 | Schiff |
| 4,576,591 A | 3/1986 | Kay et al. |
| 4,589,412 A | 5/1986 | Kensey |
| 4,641,654 A | 2/1987 | Samson et al. |
| 4,651,738 A | 3/1987 | Demer et al. |
| 4,687,465 A | 8/1987 | Prindle et al. |
| 4,723,550 A | 2/1988 | Bales et al. |
| 4,723,936 A | 2/1988 | Buchbinder et al. |
| 4,723,938 A | 2/1988 | Goodin et al. |
| 4,726,374 A | 2/1988 | Bales et al. |
| 4,758,223 A | 7/1988 | Rydell |
| 4,762,130 A | 8/1988 | Fogarty et al. |
| 4,781,192 A | 11/1988 | Demer |
| 4,784,636 A | 11/1988 | Rydell |
| 4,846,174 A | 7/1989 | Willard et al. |
| 4,848,342 A | 7/1989 | Kaltenbach |
| RE33,166 E | 2/1990 | Samson |
| 4,921,484 A | 5/1990 | Hillstead |
| 4,994,065 A | 2/1991 | Gibbs et al. |
| 5,009,659 A | 4/1991 | Hamlin et al. |
| 5,024,668 A | 6/1991 | Peters et al. |
| 5,042,707 A | 8/1991 | Taheri |
| 5,047,015 A | 9/1991 | Foote et al. |
| 5,102,390 A | 4/1992 | Crittenden et al. |
| 5,160,341 A | 11/1992 | Brenneman et al. |
| 5,196,024 A | 3/1993 | Barath |
| 5,201,757 A | 4/1993 | Heyn et al. |
| 5,242,452 A | 9/1993 | Inoue |
| 5,246,420 A | 9/1993 | Kraus et al. |
| 5,250,029 A | 10/1993 | Lin et al. |
| 5,250,060 A | 10/1993 | Carbo et al. |
| 5,263,962 A | 11/1993 | Johnson et al. |
| 5,269,758 A | 12/1993 | Taheri |
| 5,304,121 A | 4/1994 | Sahatjian |
| 5,318,529 A | 6/1994 | Kontos |
| 5,336,234 A | 8/1994 | Virgil et al. |
| 5,344,397 A | 9/1994 | Heaven et al. |
| 5,383,890 A | 1/1995 | Miraki et al. |
| 5,397,305 A | 3/1995 | Kawula et al. |
| 5,397,355 A | 3/1995 | Marin et al. |
| 5,421,955 A | 6/1995 | Lau et al. |
| 5,423,851 A | 6/1995 | Samuels |
| 5,423,885 A | 6/1995 | Williams |
| 5,443,477 A | 8/1995 | Marin et al. |
| 5,501,689 A | 3/1996 | Green et al. |
| 5,534,007 A | 7/1996 | St. Germain et al. |
| 5,536,252 A | 7/1996 | Imran et al. |
| 5,540,659 A | 7/1996 | Teirstein |
| 5,545,135 A | 8/1996 | Iacob et al. |
| 5,562,728 A | 10/1996 | Lazarus et al. |
| 5,569,272 A | 10/1996 | Reed et al. |
| 5,571,135 A | 11/1996 | Fraser et al. |
| 5,591,197 A | 1/1997 | Orth et al. |
| 5,593,417 A | 1/1997 | Rhodes |
| 5,601,568 A | 2/1997 | Chevillon et al. |
| 5,616,149 A | 4/1997 | Barath |
| 5,618,300 A | 4/1997 | Marin et al. |
| 5,634,928 A | 6/1997 | Fischell et al. |
| 5,643,312 A | 7/1997 | Fischell et al. |
| 5,645,559 A | 7/1997 | Hachtman et al. |
| 5,665,116 A | 9/1997 | Chaisson et al. |
| 5,681,346 A | 10/1997 | Orth et al. |
| 5,704,913 A | 1/1998 | Abele et al. |
| 5,707,376 A | 1/1998 | Kavteladze et al. |
| 5,725,572 A | 3/1998 | Lam et al. |
| 5,728,158 A | 3/1998 | Lau et al. |
| 5,741,270 A | 4/1998 | Hansen et al. |
| 5,743,874 A | 4/1998 | Fischell et al. |
| 5,746,716 A | 5/1998 | Vigil et al. |
| 5,746,764 A | 5/1998 | Green et al. |
| 5,776,161 A | 7/1998 | Globerman |
| 5,797,951 A | 8/1998 | Mueller |
| 5,800,526 A | 9/1998 | Anderson et al. |
| 5,813,977 A | 9/1998 | Hinchliffe et al. |
| 5,817,152 A | 10/1998 | Birdsall et al. |
| 5,829,662 A | 11/1998 | Allen et al. |
| 5,833,694 A | 11/1998 | Poncet |
| 5,843,033 A | 12/1998 | Ropiak |
| 5,911,725 A | 6/1999 | Boury |
| 5,925,061 A | 7/1999 | Ogi et al. |
| 5,928,247 A | 7/1999 | Barry et al. |
| 5,944,727 A | 8/1999 | Ahari et al. |
| 5,954,742 A | 9/1999 | Osypka |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,968,088 A | 10/1999 | Hansen et al. |
| 5,972,023 A | 10/1999 | Tanner et al. |
| 5,980,552 A | 11/1999 | Pinchasik et al. |
| 6,004,328 A | 12/1999 | Solar |
| 6,007,543 A | 12/1999 | Ellis et al. |
| 6,009,614 A | 1/2000 | Morales |
| 6,013,854 A | 1/2000 | Moriuchi |
| 6,022,374 A | 2/2000 | Imran |
| 6,036,725 A | 3/2000 | Avellanet |
| 6,048,360 A | 4/2000 | Khosravi et al. |
| 6,053,941 A | 4/2000 | Lindenberg et al. |
| 6,053,943 A | 4/2000 | Edwin et al. |
| 6,080,177 A | 6/2000 | Igaki |
| 6,090,135 A | 7/2000 | Plaia et al. |
| 6,110,198 A | 8/2000 | Fogarty et al. |
| 6,123,722 A | 9/2000 | Fogarty et al. |
| 6,126,685 A | 10/2000 | Lenker et al. |
| 6,129,754 A | 10/2000 | Kanesaka et al. |
| 6,139,573 A | 10/2000 | Sogard et al. |
| 6,143,016 A | 11/2000 | Bleam et al. |
| 6,146,358 A | 11/2000 | Rowe |
| 6,152,937 A | 11/2000 | Peterson et al. |
| 6,157,852 A | 12/2000 | Selmon et al. |
| 6,165,199 A | 12/2000 | Barbut |
| 6,187,034 B1 | 2/2001 | Frantzen |
| 6,197,013 B1 | 3/2001 | Reed |
| 6,197,103 B1 | 3/2001 | Davies et al. |
| 6,200,336 B1 | 3/2001 | Pavcnik et al. |
| 6,203,550 B1 | 3/2001 | Olson |
| 6,203,568 B1 | 3/2001 | Lombardi et al. |
| 6,203,569 B1 | 3/2001 | Wijay |
| 6,221,102 B1 | 4/2001 | Baker et al. |
| 6,238,402 B1 | 5/2001 | Sullivan et al. |
| 6,241,667 B1 | 6/2001 | Vetter et al. |
| 6,254,628 B1 | 7/2001 | Wallace et al. |
| 6,258,117 B1 | 7/2001 | Camrud et al. |

(56) References Cited

U.S. PATENT DOCUMENTS

| | | |
|---|---|---|
| 6,266,550 B1 | 7/2001 | Selmon et al. |
| 6,270,524 B1 | 8/2001 | Kim |
| 6,273,909 B1 | 8/2001 | Kugler et al. |
| 6,290,728 B1 | 9/2001 | Phelps et al. |
| 6,312,444 B1 | 11/2001 | Barbut |
| 6,312,460 B2 | 11/2001 | Drasler et al. |
| 6,325,824 B2 | 12/2001 | Limon |
| 6,331,189 B1 | 12/2001 | Wolinsky et al. |
| 6,338,739 B1 | 1/2002 | Datta et al. |
| 6,344,053 B1 | 2/2002 | Boneau |
| 6,364,901 B1 | 4/2002 | Inoue |
| 6,364,904 B1 | 4/2002 | Smith |
| 6,371,962 B1 | 4/2002 | Ellis et al. |
| 6,387,113 B1 | 5/2002 | Hawkins et al. |
| 6,391,050 B1 | 5/2002 | Broome |
| 6,402,760 B1 | 6/2002 | Fedida |
| 6,402,777 B1 | 6/2002 | Globerman |
| 6,409,752 B1 | 6/2002 | Boatman et al. |
| 6,409,863 B1 | 6/2002 | Williams et al. |
| 6,425,915 B1 | 7/2002 | Khosravi et al. |
| 6,428,550 B1 | 8/2002 | Vargas et al. |
| 6,428,566 B1 | 8/2002 | Holt |
| 6,475,237 B2 | 11/2002 | Drasler et al. |
| 6,485,507 B1 | 11/2002 | Walak et al. |
| 6,485,508 B1 | 11/2002 | McGuinness |
| 6,485,510 B1 | 11/2002 | Camrud et al. |
| 6,491,707 B2 | 12/2002 | Makower et al. |
| 6,508,822 B1 | 1/2003 | Peterson et al. |
| 6,514,261 B1 | 2/2003 | Randall et al. |
| 6,517,573 B1 | 2/2003 | Pollock et al. |
| 6,520,934 B1 | 2/2003 | Lee et al. |
| 6,520,983 B1 | 2/2003 | Colgan et al. |
| 6,520,984 B1 | 2/2003 | Garrison et al. |
| 6,527,800 B1 | 3/2003 | McGuckin, Jr. et al. |
| 6,547,817 B1 | 4/2003 | Fischell et al. |
| 6,551,353 B1 | 4/2003 | Baker et al. |
| 6,599,296 B1 | 7/2003 | Gillick et al. |
| 6,607,551 B1 * | 8/2003 | Sullivan ............ A61F 2/95 623/1.11 |
| 6,623,521 B2 | 9/2003 | Steinke et al. |
| 6,629,994 B2 | 10/2003 | Gomez et al. |
| 6,635,083 B1 | 10/2003 | Cheng et al. |
| 6,648,911 B1 | 11/2003 | Sirhan et al. |
| 6,660,031 B2 | 12/2003 | Tran et al. |
| 6,676,698 B2 | 1/2004 | McGuckin, Jr. et al. |
| 6,692,504 B2 | 2/2004 | Kurz et al. |
| 6,699,274 B2 | 3/2004 | Stinson |
| 6,699,277 B1 | 3/2004 | Freidberg et al. |
| 6,706,061 B1 | 3/2004 | Fischell et al. |
| 6,716,240 B2 | 4/2004 | Fischell et al. |
| 6,719,775 B2 | 4/2004 | Slaker et al. |
| 6,723,119 B2 | 4/2004 | Pinchasik et al. |
| 6,730,116 B1 | 5/2004 | Wolinsky et al. |
| 6,746,475 B1 | 6/2004 | Rivelli, Jr. |
| 6,752,828 B2 | 6/2004 | Thornton |
| 6,755,854 B2 | 6/2004 | Gillick et al. |
| 6,786,922 B2 | 9/2004 | Schaeffer |
| 6,790,221 B2 | 9/2004 | Monroe et al. |
| 6,790,227 B2 | 9/2004 | Burgermeister |
| 6,810,882 B2 | 11/2004 | Langberg et al. |
| 6,814,752 B1 | 11/2004 | Chuter |
| 6,827,731 B2 | 12/2004 | Armstrong et al. |
| 6,843,400 B1 | 1/2005 | Lee |
| 6,846,323 B2 | 1/2005 | Yip et al. |
| 6,849,087 B1 | 2/2005 | Chuter |
| 6,863,685 B2 | 3/2005 | Davila et al. |
| 6,866,669 B2 | 3/2005 | Buzzard et al. |
| 6,896,697 B1 | 5/2005 | Yip et al. |
| 6,899,718 B2 | 5/2005 | Gifford, III et al. |
| 6,899,914 B2 | 5/2005 | Schaldach et al. |
| 6,911,039 B2 | 6/2005 | Shiu et al. |
| 6,913,600 B2 | 7/2005 | Valley et al. |
| 6,942,680 B2 | 9/2005 | Grayzel et al. |
| 6,942,689 B2 | 9/2005 | Majercak |
| 6,945,992 B2 | 9/2005 | Goodson, IV et al. |
| 6,951,554 B2 | 10/2005 | Johansen et al. |
| 6,986,784 B1 | 1/2006 | Weiser et al. |
| 6,989,021 B2 | 1/2006 | Bosma et al. |
| 7,001,422 B2 | 2/2006 | Escamilla et al. |
| 7,001,424 B2 | 2/2006 | Patel et al. |
| 7,007,698 B2 | 3/2006 | Thornton |
| 7,018,402 B2 | 3/2006 | Vito et al. |
| 7,025,791 B2 | 4/2006 | Levine et al. |
| 7,037,330 B1 | 5/2006 | Rivelli, Jr. et al. |
| 7,041,130 B2 | 5/2006 | Santini, Jr. et al. |
| 7,052,511 B2 | 5/2006 | Weldon |
| 7,087,088 B2 | 8/2006 | Berg et al. |
| 7,105,016 B2 | 9/2006 | Shiu et al. |
| 7,122,043 B2 | 10/2006 | Greenhalgh et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,147,661 B2 | 12/2006 | Chobotov et al. |
| 7,150,745 B2 | 12/2006 | Stern et al. |
| 7,160,312 B2 | 1/2007 | Saadat |
| 7,163,552 B2 | 1/2007 | Diaz |
| 7,166,125 B1 | 1/2007 | Baker et al. |
| 7,169,158 B2 | 1/2007 | Sniffin et al. |
| 7,169,163 B2 | 1/2007 | Becker |
| 7,172,617 B2 | 2/2007 | Colgan et al. |
| 7,175,654 B2 | 2/2007 | Bonsignore et al. |
| 7,179,284 B2 | 2/2007 | Khosravi et al. |
| 7,182,779 B2 | 2/2007 | Acosta et al. |
| 7,192,440 B2 | 3/2007 | Andreas et al. |
| 7,201,770 B2 | 4/2007 | Johnson et al. |
| 7,208,002 B2 | 4/2007 | Shelso |
| 7,211,101 B2 | 5/2007 | Carley et al. |
| 7,243,408 B2 | 7/2007 | Vietmeier |
| 7,258,697 B1 | 8/2007 | Cox et al. |
| 7,261,731 B2 | 8/2007 | Patel et al. |
| 7,267,684 B2 | 9/2007 | Rolando et al. |
| 7,270,668 B2 | 9/2007 | Andreas et al. |
| 7,270,673 B2 | 9/2007 | Yee et al. |
| 7,273,492 B2 | 9/2007 | Cheng et al. |
| 7,279,007 B2 | 10/2007 | Nikolic et al. |
| 7,296,577 B2 | 11/2007 | Lashinski et al. |
| 7,300,456 B2 | 11/2007 | Andreas et al. |
| 7,294,146 B2 | 12/2007 | Chew et al. |
| 7,303,572 B2 | 12/2007 | Meisheimer et al. |
| 7,303,580 B2 | 12/2007 | Parker |
| 7,306,617 B2 | 12/2007 | Majercak |
| 7,309,341 B2 | 12/2007 | Ortiz et al. |
| 7,309,350 B2 | 12/2007 | Landreville et al. |
| 7,309,353 B2 | 12/2007 | Krivoruchko |
| 7,316,711 B2 | 1/2008 | Allen et al. |
| 7,320,702 B2 | 1/2008 | Hammersmark et al. |
| 7,323,006 B2 | 1/2008 | Andreas et al. |
| 7,323,007 B2 | 1/2008 | Sano |
| 7,326,203 B2 | 2/2008 | Papineau et al. |
| 7,326,236 B2 | 2/2008 | Andreas et al. |
| 7,329,279 B2 | 2/2008 | Haug et al. |
| 7,331,987 B1 | 2/2008 | Cox |
| 7,331,990 B2 | 2/2008 | Gianotti |
| 7,331,992 B2 | 2/2008 | Randall et al. |
| 7,351,255 B2 | 4/2008 | Andreas |
| 7,399,307 B2 | 7/2008 | Evans et al. |
| 7,402,168 B2 | 7/2008 | Sanderson et al. |
| 7,419,501 B2 | 9/2008 | Chiu et al. |
| 7,431,729 B2 | 10/2008 | Chanduszko |
| 7,445,631 B2 | 11/2008 | Salaheih et al. |
| 7,476,245 B2 | 1/2009 | Abbate |
| 7,479,158 B2 | 1/2009 | Gregorich |
| 7,500,986 B2 | 3/2009 | Lye et al. |
| 7,510,575 B2 | 3/2009 | Spenser et al. |
| 7,524,330 B2 | 4/2009 | Berreklouw |
| 7,537,607 B2 | 5/2009 | Gerberding |
| 7,550,001 B2 | 6/2009 | Dorn et al. |
| 7,553,324 B2 | 6/2009 | Andreas et al. |
| 7,556,647 B2 | 7/2009 | Drews et al. |
| 7,578,840 B2 | 8/2009 | Schaeffer |
| 7,591,848 B2 | 9/2009 | Allen |
| 7,604,662 B2 | 10/2009 | Cambronne et al. |
| 7,611,497 B2 | 11/2009 | Wollschlager |
| 7,617,007 B2 | 11/2009 | Williams et al. |

(56) References Cited

U.S. PATENT DOCUMENTS

| | | |
|---|---|---|
| 7,618,432 B2 | 11/2009 | Pedersen et al. |
| 7,618,447 B2 | 11/2009 | Case et al. |
| 7,625,398 B2 | 12/2009 | Clifford et al. |
| 7,625,399 B2 | 12/2009 | Case et al. |
| 7,628,803 B2 | 12/2009 | Pavcnik et al. |
| 7,637,935 B2 | 12/2009 | Pappas et al. |
| 7,655,033 B2 | 2/2010 | Fearnot et al. |
| 7,655,034 B2 | 2/2010 | Mitchell et al. |
| 7,658,759 B2 | 2/2010 | Case et al. |
| 7,666,216 B2 | 2/2010 | Hogendijk et al. |
| 7,674,282 B2 | 3/2010 | Wu et al. |
| 7,686,824 B2 | 3/2010 | Konstantino et al. |
| 7,686,843 B2 | 3/2010 | Moore |
| 7,695,507 B2 | 4/2010 | Rivelli, Jr. et al. |
| 7,720,521 B2 | 5/2010 | Chang et al. |
| 7,736,387 B2 | 6/2010 | Pollock et al. |
| 7,758,594 B2 | 7/2010 | Lamson et al. |
| 7,758,625 B2 | 7/2010 | Wu et al. |
| 7,758,627 B2 | 7/2010 | Richter |
| 7,758,632 B2 | 7/2010 | Hojeibane et al. |
| 7,763,063 B2 | 7/2010 | Arbefeuille et al. |
| 7,780,716 B2 | 8/2010 | Pappas et al. |
| 7,794,489 B2 | 9/2010 | Shumer et al. |
| 7,799,065 B2 | 9/2010 | Pappas |
| 7,806,918 B2 | 10/2010 | Nissl et al. |
| 7,810,223 B2 | 10/2010 | Hemerick et al. |
| 7,828,834 B2 | 11/2010 | Garbe |
| 7,833,262 B2 | 11/2010 | McGuckin, Jr. et al. |
| 7,842,080 B2 | 11/2010 | Chouinard |
| 7,846,194 B2 | 12/2010 | Hartley et al. |
| 7,867,267 B2 | 1/2011 | Sullivan et al. |
| 7,871,431 B2 | 1/2011 | Gurm et al. |
| 7,883,537 B2 | 2/2011 | Grayzel et al. |
| 7,896,911 B2 | 3/2011 | Schneider et al. |
| 7,905,913 B2 | 3/2011 | Chew et al. |
| 7,918,880 B2 | 4/2011 | Austin |
| 7,922,755 B2 | 4/2011 | Acosta et al. |
| 7,933,660 B2 | 4/2011 | Carr |
| 7,942,920 B2 | 5/2011 | Majercak |
| 7,955,315 B2 | 6/2011 | Feinberg et al. |
| 7,963,987 B2 | 6/2011 | Melsheimer et al. |
| 7,967,855 B2 | 6/2011 | Furst et al. |
| 7,971,333 B2 | 7/2011 | Gale et al. |
| 7,972,373 B2 | 7/2011 | Contiliano et al. |
| 7,981,149 B2 | 7/2011 | Contiliano et al. |
| 7,993,383 B2 | 8/2011 | Hartley et al. |
| 8,002,725 B2 | 8/2011 | Hogendijk |
| 8,016,870 B2 | 9/2011 | Chew et al. |
| 8,024,851 B2 | 9/2011 | Barr et al. |
| 8,034,099 B2 | 10/2011 | Pellegrini |
| 8,043,354 B2 | 10/2011 | Greenberg et al. |
| 8,043,357 B2 | 10/2011 | Hartley |
| 8,048,151 B2 | 11/2011 | O'Brien et al. |
| 8,052,738 B2 | 11/2011 | Craven |
| 8,057,543 B2 | 11/2011 | O'Brien et al. |
| 8,062,344 B2 | 11/2011 | Dorn et al. |
| 8,075,607 B2 | 12/2011 | Melsheimer et al. |
| 8,092,468 B2 | 1/2012 | Hansen |
| 8,100,958 B2 | 1/2012 | Fischer et al. |
| 8,127,422 B2 | 3/2012 | Wu |
| 8,128,677 B2 | 3/2012 | Schneider et al. |
| 8,157,851 B2 | 4/2012 | Andreas |
| 8,157,857 B2 | 4/2012 | Case et al. |
| 8,177,831 B2 | 5/2012 | Andreas |
| 8,221,489 B2 | 7/2012 | Issenmann et al. |
| 8,236,044 B2 | 8/2012 | Robaina |
| 8,236,045 B2 | 8/2012 | Benichou et al. |
| 8,292,938 B2 | 10/2012 | Case |
| 8,308,790 B2 | 11/2012 | Arbefeuille et al. |
| 8,317,859 B2 | 11/2012 | Snow et al. |
| 8,323,243 B2 | 12/2012 | Schneider et al. |
| 8,328,864 B2 | 12/2012 | Niermann |
| 8,353,945 B2 | 1/2013 | Andreas et al. |
| 8,366,766 B2 | 2/2013 | Berreklouw |
| 8,382,813 B2 | 2/2013 | Shumer |
| 8,394,139 B2 | 3/2013 | Roeder et al. |
| 8,403,978 B2 | 3/2013 | Schlun et al. |
| 8,409,267 B2 | 4/2013 | Berez et al. |
| 8,414,636 B2 | 4/2013 | Nabulsi et al. |
| 8,414,637 B2 | 4/2013 | Chouinard |
| 8,460,357 B2 | 6/2013 | McGarry et al. |
| 8,474,460 B2 | 7/2013 | Barrett et al. |
| 8,486,128 B2 | 7/2013 | Jen et al. |
| 8,486,132 B2 | 7/2013 | Snow et al. |
| 8,496,698 B2 | 7/2013 | Abunassar |
| 8,500,787 B2 | 8/2013 | Simpson et al. |
| 8,500,789 B2 | 8/2013 | Wuebbeling et al. |
| 8,523,935 B2 | 9/2013 | Fliedner |
| 8,540,760 B2 | 9/2013 | Paul, Jr. et al. |
| 8,585,747 B2 | 11/2013 | Andreas et al. |
| 8,636,793 B2 | 1/2014 | Hoerstrup et al. |
| 8,641,755 B2 | 2/2014 | Davis et al. |
| 8,652,198 B2 | 2/2014 | Andreas et al. |
| 8,663,310 B2 | 3/2014 | Greenberg et al. |
| 8,734,502 B2 | 5/2014 | Orr |
| 8,740,973 B2 | 6/2014 | Furst et al. |
| 8,745,842 B2 | 6/2014 | Wu |
| 8,771,335 B2 | 7/2014 | Griego et al. |
| 8,778,010 B2 | 7/2014 | Venturelli et al. |
| 8,784,467 B2 | 7/2014 | Connelly et al. |
| 8,834,556 B2 | 9/2014 | Papp et al. |
| 8,864,811 B2 | 10/2014 | Kao |
| 8,888,834 B2 | 11/2014 | Hansen et al. |
| 8,888,841 B2 | 11/2014 | Pandelidis et al. |
| 8,900,289 B2 | 12/2014 | Thompson |
| 8,911,487 B2 | 12/2014 | Bennett et al. |
| 8,926,689 B2 | 1/2015 | Bogert |
| 8,956,398 B2 | 2/2015 | George et al. |
| 8,961,583 B2 | 2/2015 | Hojeibane et al. |
| 8,966,736 B2 | 3/2015 | Wu |
| 8,968,383 B1 | 3/2015 | Johnson et al. |
| 8,969,383 B2 * | 3/2015 | Noguchi ............ A61K 31/4433 514/235.5 |
| 8,986,362 B2 | 3/2015 | Snow et al. |
| 9,005,265 B2 | 4/2015 | Lootz et al. |
| 9,005,274 B2 | 4/2015 | Seguin et al. |
| 9,023,095 B2 | 5/2015 | Bueche et al. |
| 9,050,181 B2 | 6/2015 | Hartley |
| 9,056,351 B2 | 6/2015 | Krivoruchko et al. |
| 9,095,461 B2 | 8/2015 | Schaeffer |
| 9,101,500 B2 | 8/2015 | Feld et al. |
| 9,101,503 B2 | 8/2015 | Lowe et al. |
| 9,101,506 B2 | 8/2015 | Arbefeuille et al. |
| 9,113,999 B2 | 8/2015 | Taylor et al. |
| 9,119,717 B2 | 9/2015 | Wang et al. |
| 9,125,765 B2 | 9/2015 | Melsheimer |
| 9,149,379 B2 | 10/2015 | Keady et al. |
| 9,192,492 B2 | 11/2015 | Seguin et al. |
| 9,192,496 B2 | 11/2015 | Robinson |
| 9,198,783 B2 | 12/2015 | Douk et al. |
| 9,216,082 B2 | 12/2015 | Von Segesser et al. |
| 9,237,959 B2 | 1/2016 | Cage |
| 9,241,702 B2 | 1/2016 | Maisano et al. |
| 9,301,864 B2 | 4/2016 | Kao |
| 9,314,327 B2 | 4/2016 | Orr |
| 9,314,360 B2 | 4/2016 | Kao |
| 9,339,404 B2 | 5/2016 | Snow et al. |
| 9,345,597 B2 | 5/2016 | Pacetti |
| 9,364,350 B2 | 6/2016 | Pacetti et al. |
| 9,370,437 B2 | 6/2016 | Chuter et al. |
| 9,375,327 B2 | 6/2016 | Giasolli et al. |
| 9,375,336 B1 | 6/2016 | Longo et al. |
| 9,398,967 B2 | 7/2016 | Cornelius |
| 9,408,731 B2 | 8/2016 | Hartley et al. |
| 9,421,115 B2 | 8/2016 | Wübbeling et al. |
| 9,427,340 B2 | 8/2016 | Yadin |
| 9,439,795 B2 | 9/2016 | Wang et al. |
| 9,445,929 B2 | 9/2016 | Longo et al. |
| 9,452,067 B2 | 9/2016 | Wu |
| 9,480,826 B2 | 11/2016 | Schneider et al. |
| 9,498,296 B2 | 11/2016 | Hingston et al. |
| 9,498,322 B2 | 11/2016 | Thomas |
| 9,539,130 B2 | 1/2017 | Farag et al. |
| 9,545,322 B2 | 1/2017 | Schneider et al. |

(56) References Cited

U.S. PATENT DOCUMENTS

| | | |
|---|---|---|
| 9,566,179 B2 | 2/2017 | Andreas et al. |
| 9,585,777 B2 | 3/2017 | Pacetti |
| 9,597,213 B2 | 3/2017 | Green |
| 9,603,696 B2 | 3/2017 | Hartley et al. |
| 9,603,730 B2 | 3/2017 | Giasolli et al. |
| 9,603,980 B2 | 3/2017 | Zhao |
| 9,662,231 B2 | 5/2017 | Ngo et al. |
| 9,668,892 B2 | 6/2017 | Shalev et al. |
| 9,700,448 B2 | 7/2017 | Snow et al. |
| 9,707,115 B2 | 7/2017 | Masakazu |
| 9,724,224 B2 | 8/2017 | Gillick et al. |
| 9,730,818 B2 | 8/2017 | Giasolli et al. |
| 9,737,368 B2 | 8/2017 | Lumauig |
| 9,867,699 B2 | 1/2018 | Straubinger et al. |
| 9,877,828 B2 | 1/2018 | Straubinger et al. |
| 9,895,243 B2 | 2/2018 | Kariniemi et al. |
| 9,908,297 B2 | 3/2018 | Pacetti et al. |
| 9,918,835 B2 | 3/2018 | Guyenot et al. |
| 9,943,428 B2 | 4/2018 | Burkart et al. |
| 9,974,670 B2 | 5/2018 | Schneider et al. |
| 9,987,154 B2 | 6/2018 | Pacetti et al. |
| 10,022,250 B2 | 7/2018 | Giasolli et al. |
| 10,098,764 B2 | 10/2018 | Pacetti |
| 10,111,741 B2 | 10/2018 | Michalak |
| 10,117,762 B2 | 11/2018 | Giasolli et al. |
| 10,137,013 B2 | 11/2018 | Giasolli et al. |
| 10,166,127 B2 | 1/2019 | Giasolli et al. |
| 10,188,533 B2 | 1/2019 | Schneider et al. |
| 10,231,853 B2 | 3/2019 | Weber |
| 10,231,854 B2 | 3/2019 | Wack |
| 10,238,339 B2 | 3/2019 | Dlugach et al. |
| 10,245,167 B2 | 4/2019 | Longo |
| 10,245,168 B2 | 4/2019 | Amendt et al. |
| 10,271,973 B2 | 4/2019 | Giasolli et al. |
| 10,278,839 B2 | 5/2019 | Giasolli et al. |
| 10,285,831 B2 | 5/2019 | Giasolli et al. |
| 10,292,845 B2 | 5/2019 | Higashi et al. |
| 10,299,945 B2 | 5/2019 | Schneider et al. |
| 10,390,977 B2 | 8/2019 | Giasolli et al. |
| 10,660,771 B2 | 5/2020 | Giasolli et al. |
| 2002/0099435 A1* | 7/2002 | Stinson ............ A61F 2/90 623/1.12 |
| 2002/0120323 A1 | 8/2002 | Thompson |
| 2002/0123790 A1 | 9/2002 | White et al. |
| 2002/0165599 A1 | 11/2002 | Nasralla |
| 2002/0169495 A1 | 11/2002 | Gifford et al. |
| 2003/0055491 A1 | 3/2003 | Schwartz et al. |
| 2003/0069630 A1 | 4/2003 | Burgermeister et al. |
| 2003/0130720 A1 | 7/2003 | DePalma et al. |
| 2003/0220683 A1 | 11/2003 | Minasian et al. |
| 2003/0225446 A1 | 12/2003 | Hartley |
| 2003/0225448 A1 | 12/2003 | Gerberding |
| 2004/0010307 A1 | 1/2004 | Grad et al. |
| 2004/0059407 A1* | 3/2004 | Escamilla ........ A61B 17/12022 623/1.12 |
| 2004/0098081 A1* | 5/2004 | Landreville ............ A61F 2/91 623/1.11 |
| 2004/0186551 A1 | 9/2004 | Kao et al. |
| 2004/0186558 A1 | 9/2004 | Pavcnik et al. |
| 2004/0215324 A1 | 10/2004 | Vonderwalde et al. |
| 2004/0260389 A1 | 12/2004 | Case et al. |
| 2004/0267281 A1 | 12/2004 | Harari et al. |
| 2004/0267348 A1 | 12/2004 | Gunderson et al. |
| 2005/0010275 A1 | 1/2005 | Sahatjian et al. |
| 2005/0021123 A1 | 1/2005 | Dorn et al. |
| 2005/0096731 A1 | 5/2005 | Looi et al. |
| 2005/0149163 A1 | 7/2005 | Sahota |
| 2005/0246008 A1 | 11/2005 | Hogendijk et al. |
| 2005/0251164 A1 | 11/2005 | Gifford, III et al. |
| 2005/0273151 A1 | 12/2005 | Fulkerson |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0047297 A1 | 3/2006 | Case |
| 2006/0069424 A1 | 3/2006 | Acosta et al. |
| 2006/0074478 A1 | 4/2006 | Feller, III |
| 2006/0111769 A1 | 5/2006 | Murray |
| 2006/0184225 A1 | 8/2006 | Pryor |
| 2006/0184227 A1 | 8/2006 | Rust |
| 2006/0206190 A1 | 9/2006 | Chermoni |
| 2006/0248698 A1 | 11/2006 | Hanson et al. |
| 2006/0265040 A1* | 11/2006 | Murray ............ A61F 2/958 623/1.11 |
| 2006/0282149 A1 | 12/2006 | Kao |
| 2007/0088420 A1 | 4/2007 | Andreas et al. |
| 2007/0093744 A1 | 4/2007 | Elmaleh |
| 2007/0142892 A1 | 6/2007 | Dave et al. |
| 2007/0156223 A1 | 7/2007 | Vaughan |
| 2007/0156224 A1 | 7/2007 | Cioanta et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0191926 A1 | 8/2007 | Nikanorov et al. |
| 2007/0233235 A1 | 10/2007 | Chouinard |
| 2008/0033522 A1 | 2/2008 | Grewe et al. |
| 2008/0051867 A1 | 2/2008 | Davila et al. |
| 2008/0077229 A1 | 3/2008 | Andreas et al. |
| 2008/0082154 A1 | 4/2008 | Tseng et al. |
| 2008/0132999 A1 | 6/2008 | Mericle et al. |
| 2008/0188207 A1 | 8/2008 | Lee |
| 2008/0208327 A1 | 8/2008 | Rowe |
| 2008/0221658 A1 | 9/2008 | Martin et al. |
| 2008/0255653 A1 | 10/2008 | Schkolnik |
| 2008/0264102 A1 | 10/2008 | Berra |
| 2008/0269865 A1 | 10/2008 | Snow et al. |
| 2008/0319528 A1 | 12/2008 | Yribarren et al. |
| 2009/0076594 A1 | 3/2009 | Sabaria |
| 2009/0082841 A1 | 3/2009 | Zacharias et al. |
| 2009/0099641 A1 | 4/2009 | Wu et al. |
| 2009/0149943 A1 | 6/2009 | Tower |
| 2009/0214615 A1 | 8/2009 | Zhao |
| 2009/0216284 A1 | 8/2009 | Chin et al. |
| 2009/0248139 A1 | 10/2009 | Pellegrini |
| 2009/0248141 A1 | 10/2009 | Shandas et al. |
| 2009/0270965 A1 | 10/2009 | Sinha et al. |
| 2009/0270967 A1 | 10/2009 | Fleming, III et al. |
| 2009/0276031 A1 | 11/2009 | Kao |
| 2010/0042121 A1 | 2/2010 | Schneider et al. |
| 2010/0131045 A1 | 5/2010 | Globerman et al. |
| 2010/0137966 A1 | 6/2010 | Magnuson |
| 2010/0145431 A1 | 6/2010 | Wu et al. |
| 2010/0228333 A1 | 9/2010 | Drasler et al. |
| 2010/0318173 A1 | 12/2010 | Kolandaivelu et al. |
| 2011/0004237 A1 | 1/2011 | Schneider et al. |
| 2011/0077731 A1 | 3/2011 | Lee et al. |
| 2011/0125248 A1 | 5/2011 | George et al. |
| 2011/0152992 A1 | 6/2011 | Schneider et al. |
| 2011/0230954 A1 | 9/2011 | Schneider et al. |
| 2011/0307049 A1* | 12/2011 | Kao ............ A61F 2/966 623/1.11 |
| 2012/0016457 A1 | 1/2012 | Chobotov et al. |
| 2012/0035705 A1 | 2/2012 | Giasolli et al. |
| 2012/0065722 A1 | 3/2012 | Pacetti |
| 2012/0083872 A1 | 4/2012 | Schneider et al. |
| 2012/0172963 A1 | 7/2012 | Ryan et al. |
| 2012/0191176 A1 | 7/2012 | Nagl et al. |
| 2012/0226343 A1 | 9/2012 | Vo et al. |
| 2012/0283811 A1 | 11/2012 | Neilan |
| 2013/0144375 A1 | 6/2013 | Giasolli et al. |
| 2014/0081380 A1 | 3/2014 | Giasolli et al. |
| 2014/0088565 A1 | 3/2014 | Vongphakdy et al. |
| 2014/0194967 A1 | 7/2014 | Schneider et al. |
| 2014/0288629 A1 | 9/2014 | Amendt |
| 2015/0297378 A1 | 10/2015 | Senness et al. |
| 2016/0192942 A1 | 7/2016 | Strauss et al. |
| 2016/0220401 A1 | 8/2016 | Longo et al. |
| 2016/0242943 A1 | 8/2016 | Riedy et al. |
| 2017/0000629 A1 | 1/2017 | Giasolli et al. |
| 2017/0181873 A1 | 6/2017 | Schneider et al. |
| 2017/0231751 A1 | 8/2017 | Barthold et al. |
| 2017/0281375 A1 | 10/2017 | Longo et al. |
| 2017/0296366 A1 | 10/2017 | Giasolli et al. |
| 2017/0319361 A1 | 11/2017 | Giasolli et al. |
| 2017/0319364 A1 | 11/2017 | Jung et al. |

(56) References Cited

U.S. PATENT DOCUMENTS

| | | |
|---|---|---|
| 2017/0367856 A1 | 12/2017 | Tanaka et al. |
| 2018/0028306 A1 | 2/2018 | Gonzalez et al. |
| 2018/0110634 A1 | 4/2018 | Giasolli et al. |
| 2018/0154123 A1 | 6/2018 | Werneth et al. |
| 2018/0200085 A1 | 7/2018 | Giasolli et al. |
| 2018/0200086 A1 | 7/2018 | Giasolli et al. |
| 2018/0200087 A1 | 7/2018 | Giasolli et al. |
| 2018/0207008 A1 | 7/2018 | Giasolli et al. |
| 2018/0272044 A1 | 9/2018 | Hossainy et al. |
| 2018/0303640 A1 | 10/2018 | Schneider et al. |
| 2018/0318116 A1 | 11/2018 | Eli et al. |
| 2019/0069985 A1 | 3/2019 | Nennig et al. |
| 2019/0070025 A1 | 3/2019 | Fu et al. |
| 2019/0192319 A1 | 6/2019 | Giasolli et al. |
| 2019/0192321 A1 | 6/2019 | Schneider et al. |
| 2019/0282381 A1 | 9/2019 | Giasolli et al. |

FOREIGN PATENT DOCUMENTS

| | | |
|---|---|---|
| AU | 2014201067 | 3/2014 |
| AU | 2010259907 | 8/2015 |
| AU | 2013212056 | 7/2016 |
| AU | 2015207895 | 5/2017 |
| AU | 2014280976 | 7/2017 |
| CA | 2705275 | 7/2013 |
| CN | 1856280 | 11/2006 |
| CN | 101102728 | 1/2008 |
| CN | 101262835 | 9/2008 |
| CN | 101754727 | 6/2010 |
| CN | 101909552 | 12/2010 |
| CN | 102292036 | 12/2011 |
| CN | 102573701 | 7/2012 |
| CN | 102724931 | 10/2012 |
| CN | 103313682 | 9/2013 |
| CN | 104220026 | 12/2014 |
| CN | 104887365 | 9/2015 |
| CN | 103313682 | 8/2016 |
| CN | 104220026 | 9/2016 |
| CN | 106466205 | 3/2017 |
| CN | 106473786 | 3/2017 |
| CN | 106473849 | 3/2017 |
| CN | 107028691 | 8/2017 |
| CN | 107157632 | 9/2017 |
| CN | 107205834 | 9/2017 |
| CN | 104887365 | 12/2017 |
| CN | 107427375 | 12/2017 |
| DE | 60030705 | 5/2007 |
| DE | 10 2009 041 025 | 3/2011 |
| DE | 20 2011 107 781 | 12/2011 |
| DE | 20 2011 110 714 | 12/2015 |
| DE | 10 2014 016 588 | 5/2016 |
| DE | 20 2011 110 818 | 9/2016 |
| DK | 2775968 | 12/2017 |
| EP | 0497620 | 8/1992 |
| EP | 0714640 | 6/1996 |
| EP | 0855883 | 8/1998 |
| EP | 0812580 | 2/2004 |
| EP | 1393766 | 3/2004 |
| EP | 1236446 | 8/2005 |
| EP | 1803423 | 7/2007 |
| EP | 1894545 | 3/2008 |
| EP | 1452151 | 10/2008 |
| EP | 1567093 | 1/2009 |
| EP | 1378212 | 9/2009 |
| EP | 2219535 | 8/2010 |
| EP | 2440155 | 4/2012 |
| EP | 1729682 | 4/2013 |
| EP | 1786367 | 4/2013 |
| EP | 1973502 | 4/2014 |
| EP | 2806826 | 12/2014 |
| EP | 2881086 | 6/2015 |
| EP | 2699207 | 10/2015 |
| EP | 2590602 | 12/2015 |
| EP | 3015078 | 5/2016 |
| EP | 3058900 | 8/2016 |
| EP | 1689327 | 9/2016 |
| EP | 3072463 | 9/2016 |
| EP | 2775968 | 9/2017 |
| EP | 3217927 | 9/2017 |
| EP | 2967830 | 11/2017 |
| EP | 3250159 | 12/2017 |
| EP | 3421010 | 1/2019 |
| FR | 2714816 | 7/1995 |
| GB | 201106757 | 6/2011 |
| JP | H06-000221 | 1/1994 |
| JP | H08-332229 | 12/1996 |
| JP | H11-501526 | 2/1999 |
| JP | H11-506665 | 6/1999 |
| JP | 2002-513298 | 5/2002 |
| JP | 2007-503923 | 3/2007 |
| JP | 2007-504897 | 3/2007 |
| JP | 2007-508112 | 4/2007 |
| JP | 2008-504078 | 2/2008 |
| JP | 2008-507376 | 3/2008 |
| JP | 2008-510587 | 4/2008 |
| JP | 2008-246214 | 10/2008 |
| JP | 2008-537891 | 10/2008 |
| JP | 2009-532115 | 9/2009 |
| JP | 2010-516333 | 5/2010 |
| JP | 2012-523922 | 10/2012 |
| JP | 2015-506760 | 3/2015 |
| JP | 2016-135278 | 7/2016 |
| JP | 2016-147051 | 8/2016 |
| JP | 6006808 | 10/2016 |
| KR | 10-2017-0084214 | 7/2017 |
| WO | WO 1996/002211 | 2/1996 |
| WO | WO 1996/009013 | 3/1996 |
| WO | WO 1996/037167 | 11/1996 |
| WO | WO 1998/007390 | 2/1998 |
| WO | WO 1999/048440 | 9/1999 |
| WO | WO 1999/049440 | 9/1999 |
| WO | WO 2000/066034 | 11/2000 |
| WO | WO 2001/076509 | 10/2001 |
| WO | WO 2002/034163 | 5/2002 |
| WO | WO 2003/047651 | 6/2003 |
| WO | WO 2003/101310 | 12/2003 |
| WO | WO 2004/006983 | 1/2004 |
| WO | WO 2004/032799 | 4/2004 |
| WO | WO 2005/039449 | 5/2005 |
| WO | WO 2006/005082 | 1/2006 |
| WO | WO 2006/014767 | 2/2006 |
| WO | WO 2006/026371 | 3/2006 |
| WO | WO 2006/026377 | 3/2006 |
| WO | WO 2006/110258 | 10/2006 |
| WO | WO 2007/088549 | 8/2007 |
| WO | WO 2007/109621 | 9/2007 |
| WO | WO 2007/118005 | 10/2007 |
| WO | WO 2009/076517 | 6/2009 |
| WO | WO 2010/037141 | 4/2010 |
| WO | WO 2010/118432 | 10/2010 |
| WO | WO 2010/144845 | 12/2010 |
| WO | WO 2011/153110 | 12/2011 |
| WO | WO 2012/006602 | 1/2012 |
| WO | WO 2012/143731 | 10/2012 |
| WO | WO 2013/068127 | 5/2013 |
| WO | WO 2013/112768 | 8/2013 |
| WO | WO 2004/091441 | 10/2014 |
| WO | WO 2016/074799 | 5/2016 |
| WO | WO 2016/122947 | 8/2016 |
| WO | WO 2018/175048 | 9/2018 |

OTHER PUBLICATIONS

Bosiers, M. et al., "Results from the Tack Optimized Balloon Angioplasty (TOBA) study demonstrate the benefits of minimal metal implants for dissection repair after angioplasty", Journal of Vascular Surgery, vol. 64, Jul. 2016, in 8 pages.

Kokkinidis, D. et al., "Emerging and Future Therapeutic Options for Femoropopliteal and Infrapopliteal Endovascular Intervention", Interventional Cardiology Clinics, vol. 6, 2017, in 17 pages.

Shishehbor, M. et al., "Endovascular Treatment of Femoropopliteal Lesions", Journal of the American College of Cardiology, vol. 66, 2015, in 4 pages.

(56) References Cited

OTHER PUBLICATIONS

Zeller, T. et al., "Novel Approaches to the Management of Advanced Peripheral Artery Disease: Perspectives on Drug-Coated Balloons, Drug-Eluting Stents, and Bioresorbable Scaffolds", Current Cardiology Reports, vol. 17, Sep. 2015, in 6 pages.
International Preliminary Report on Patentability, re PCT Application No. PCT/US2008/086396, dated Jun. 15, 2010.
International Preliminary Report on Patentability, re PCT Application No. PCT/US2011/038468, dated Dec. 13, 2012.
International Preliminary Report on Patentability, re PCT Application No. PCT/US2011/043471, dated Jan. 17, 2013.
International Preliminary Report on Patentability, re PCT Application No. PCT/US2013/023030, dated Aug. 7, 2014.
Colombo et al., "Intravascular Ultrasound-Guided Percutaneous Transluminal Coronary Angioplasty With Provisional Spot Stenting for Treatment of Long Coronary Lesions", Journal of the American College of Cardiology, vol. 38, No. 5, Nov. 1, 2001.
Mosseri et al., "New Indicator for Stent Covering Area", in Catheterization and Cardiovascular Diagnosis, 1998, vol. 44, pp. 188-192.
Australian Office Action (Notice of Acceptance), re AU Application No. 2011274392, dated Nov. 14, 2013, including accepted (allowed) claims.
Australian Office Action, re AU Application No. 2008335140, dated Apr. 21, 2011.
Australian Office Action, re AU Application No. 2008335140, dated Mar. 15, 2011.
Australian Office Action, re AU Application No. 2011274392, dated May 3, 2013.
European Office Action and Supplemental European Search Report, re EP Application No. 11804455.1, dated Jun. 11, 2014.
European Office Action and Supplementary Partial European Search Report, re EP Application No. 08858824.9, dated Sep. 27, 2012.
International Search Report and Written Opinion, re PCT Application No. PCT/US2010/038379, dated Feb. 25, 2011.
International Search Report and Written Opinion, re PCT Application No. PCT/US2011/038468, dated Jan. 18, 2012.
International Search Report and Written Opinion, re PCT Application No. PCT/US2013/023030, dated Apr. 16, 2013.
International Search Report and Written Opinion, re PCT Application PCT/US2008/086396, dated Jul. 27, 2009.
International Search Report and Written Opinion, re PCT Application PCT/US2011/043471, dated Feb. 9, 2012.
International Search Report, re PCT Application No. PCT/US2013/023030, dated Apr. 16, 2013.
Japanese Office Action and translation in Japanese Patent Application No. 2016-014565 dated Feb. 3, 2017 in 12 pages.
English translation of the first Office Action and Search Report in Chinese Application No. 201610546800.2 in 5 pages dated Sep. 28, 2017.
English translation of the first Office Action and Search Report in Chinese Application No. 201610546643.5 in 5 pages dated Oct. 17, 2017.
U.S. Appl. No. 15/921,464, filed Mar. 14, 2018, Deployment Device for Placement of Multiple Intraluminal Surgical Staples.
U.S. Appl. No. 15/921,459, filed Mar. 14, 2018, Endovascular Implant.
U.S. Appl. No. 15/415,167, filed Jan. 25, 2017, Delivery Device and Method of Delivery.
U.S. Appl. No. 13/038,175 (U.S. Pat. No. 9,545,322), filed Mar. 1, 2011 (Jan. 17, 2017), Device and Method for Tacking Plaque to Blood Vessel Wall.
U.S. Appl. No. 16/998,168, filed Aug. 20, 2020, Device and Method for Tacking Plaque to Blood Vessel Wall.
U.S. Appl. No. 16/998,190, filed Aug. 20, 2020, Endovascular Implant.
U.S. Appl. No. 16/998,196, filed Aug. 20, 2020, Endoluminal Device and Method.
U.S. Appl. No. 15/914,410, filed Jun. 27, 2016, Delivery Device and Method of Delivery.
U.S. Appl. No. 11/955,331 (U.S. Pat. No. 7,896,911), filed Dec. 12, 2007 (Mar. 1, 2011), (Device and Method for Tacking Plaque to Blood Vessel Wall.
U.S. Appl. No. 13/038,175 (U.S. Pat. No. 9,545,322), filed Mar. 1, 2011 (Mar. 1, 2011), Device and Method for Tacking Plaque to Blood Vessel Wall.
U.S. Appl. No. 15/375,026, filed Dec. 9, 2016, Device and Method for Tacking Plaque to Blood Vessel Wall.
U.S. Appl. No. 12/483,193 (U.S. Pat. No. 8,128,677), filed Jun. 11, 2009 (Mar. 6, 2012), Device and Method for Tacking Plaque to a Blood Vessel Wall.
U.S. Appl. No. 13/246,776 (U.S. Pat. No. 9,974,670), filed Sep. 27, 2011, (May 22, 2018), Method of Treating Atherosclerotic Occlusive Disease.
U.S. Appl. No. 15/984,111 (U.S. Pat. No. 10,299,945), filed May 18, 2018, (May 28, 2019), Method of Treating Atherosclerotic Occlusive Disease.
U.S. Appl. No. 14/102,411, filed Dec. 10, 2013, Method of Treating Atherosclerotic Occlusive Disease.
U.S. Appl. No. 12/790,819 (U.S. Pat. No. 10,188,533), filed May 29, 2010 (Jan. 29, 2019), Minimal Surface Area Contact Device for Holding Plaque to Blood Vessel Wall.
U.S. Appl. No. 16/259,146, filed Jan. 28, 2019, Minimal Surface Area Contact Device for Holding Plaque to Blood Vessel Wall.
U.S. Appl. No. 13/118,388, filed May 28, 2011, Stent Device Having Focal Elevating Elements for Minimal Surface Area Contact With Lumen Walls.
U.S. Appl. No. 13/179,458 (U.S. Pat. No. 10,022,250), filed Jul. 8, 2011 (Jul. 17, 2018), Deployment Device for Placement of Multiple Intraluminal Surgical Staples.
U.S. Appl. No. 15/815,515, filed Nov. 16, 2017, Deployment Device for Placement of Multiple Intraluminal Surgical Staples.
U.S. Appl. No. 15/921,464 (U.S. Pat. No. 10,660,771), filed Mar. 14, 2018 (May 26, 2020), Deployment Device for Placement of Multiple Intraluminal Surgical Staples.
U.S. Appl. No. 16/881,385, filed May 22, 2020, Deployment Device for Placement of Multiple Intraluminal Surgical Staples.
U.S. Appl. No. 13/153,257 (U.S. Pat. No. 9,375,327), filed Jun. 3, 2011 (Jun. 28, 2016), Endovascular Implant.
U.S. Appl. No. 15/170,772 (U.S. Pat. No. 10,278,839), filed Jun. 1, 2016 (May 7, 2019), Endovascular Implant.
U.S. Appl. No. 15/640,095, filed Jun. 30, 2017, Endovascular Implant.
U.S. Appl. No. 15/921,448 (U.S. Pat. No. 10,285,831), filed Mar. 14, 2018 (May 14, 2019), Endovascular Implant.
U.S. Appl. No. 15/921,459 (U.S. Pat. No. 10,390,977), filed Mar. 14, 2018 (Aug. 27, 2019), Endovascular Implant.
U.S. Appl. No. 15/921,477 (U.S. Pat. No. 10,271,973), filed Mar. 14, 2018 (Apr. 30, 2019), Endovascular Implant.
U.S. Appl. No. 16/426,627, filed May 30, 2019, Endovascular Implant and Deployment Devices.
U.S. Appl. No. 13/749,643 (U.S. Pat. No. 9,730,818), filed Jan. 24, 2013 (Aug. 15, 2017), Endoluminal Device and Method.
U.S. Appl. No. 14/089,703 (U.S. Pat. No. 9,603,730), filed Nov. 25, 2013 (Mar. 28, 2017), Endoluminal Device and Method.
U.S. Appl. No. 15/472,215, filed Mar. 28, 2017, Endoluminal Device and Method.
U.S. Appl. No. 15/654,586 (U.S. Pat. No. 10,117,762), filed Jul. 19, 2017 (Nov. 6, 2018), Endoluminal Device and Method.
U.S. Appl. No. 15/837,870 (U.S. Pat. No. 10,137,013), filed Dec. 11, 2017 (Nov. 27, 2018), Endoluminal Device and Method.
U.S. Appl. No. 15/921,541 (U.S. Pat. No. 10,166,127), filed Mar. 14, 2018 (Jan. 1, 2019), Endoluminal Device and Method.
U.S. Appl. No. 16/225,528, filed Dec. 19, 2018, Endoluminal Device and Method.
U.S. Appl. No. 13/939,019, filed Jul. 10, 2013, Systems and Methods for Attaching Radiopaque Markers to a Medical Device.
U.S. Appl. No. 14/746,636 (U.S. Pat. No. 9,192,500), filed Jun. 22, 2015 (Nov. 24, 2015), Delivery Device and Method of Delivery.
U.S. Appl. No. 14/885,295 (U.S. Pat. No. 9,375,337), filed Oct. 16, 2015 (Jun. 28, 2016), Delivery Device and Method of Delivery.
U.S. Appl. No. 15/133,709, filed Apr. 20, 2016, Delivery Device and Method of Delivery.

(56) References Cited

OTHER PUBLICATIONS

U.S. Appl. No. 14/935,087 (U.S. Pat. No. 9,345,603), filed Nov. 6, 2015 (May 24, 2016), Delivery Device and Method of Delivery.
U.S. Appl. No. 15/133,751 (U.S. Pat. No. 9,602,786), filed Apr. 20, 2016 (Mar. 21, 2017), Delivery Device and Method of Delivery.
U.S. Appl. No. 14/935,121 (U.S. Pat. No. 9,320,632), filed Nov. 6, 2015 (Apr. 26, 2016), Delivery Device and Method of Delivery.
U.S. Appl. No. 15/133,158 (U.S. Pat. No. 9,584,777), filed Apr. 19, 2016 (Feb. 28, 2017), Delivery Device and Method of Delivery.
U.S. Appl. No. 15/011,321 (U.S. Pat. No. 9,456,914), filed Jan. 29, 2016 (Oct. 4, 2016), Delivery Device and Method of Delivery.
U.S. Appl. No. 15/134,315 (U.S. Pat. No. 9,585,782), filed Apr. 20, 2016 (Mar. 7, 2017), Delivery Device and Method of Delivery.
U.S. Appl. No. 15/415,167 (U.S. Pat. No. 10,610,392), filed Jan. 25, 2017 (Apr. 7, 2020), Delivery Device and Method of Delivery.
U.S. Appl. No. 16/821,578, filed Mar. 17, 2020, Delivery Device and Method of Delivery.
U.S. Appl. No. 14/656,462 (U.S. Pat. No. 9,375,336), filed Mar. 12, 2015 (Jun. 28, 2016), Delivery Device and Method of Delivery.
U.S. Appl. No. 14/935,154 (U.S. Pat. No. 9,445,929), filed Nov. 6, 2015 (Sep. 20, 2016), Delivery Device and Method of Delivery.
U.S. Appl. No. 15/194,410, filed Jun. 27, 2016, Delivery Device and Method of Delivery.
U.S. Appl. No. 15/000,437 (U.S. Pat. No. 9,433,520), filed Jan. 19, 2016 (Sep. 6, 2016), Delivery Device and Method of Delivery.
U.S. Appl. No. 15/227,757 (U.S. Pat. No. 10,245,167), filed Aug. 3, 2016 (Apr. 2, 2019), Delivery Device and Method of Delivery.
U.S. Appl. No. 16/372,224, filed Apr. 1, 2019, Delivery Device and Method of Delivery.
U.S. Appl. No. 16/067,082, filed Jun. 28, 2018, Delivery Device and Method of Delivery.
U.S. Appl. No. 15/705,793, filed Sep. 15, 2017, Delivery Device and Method of Delivery.
U.S. Appl. No. 16/632,841, filed Jan. 21, 2020, Delivery Device and Method of Delivery.

\* cited by examiner

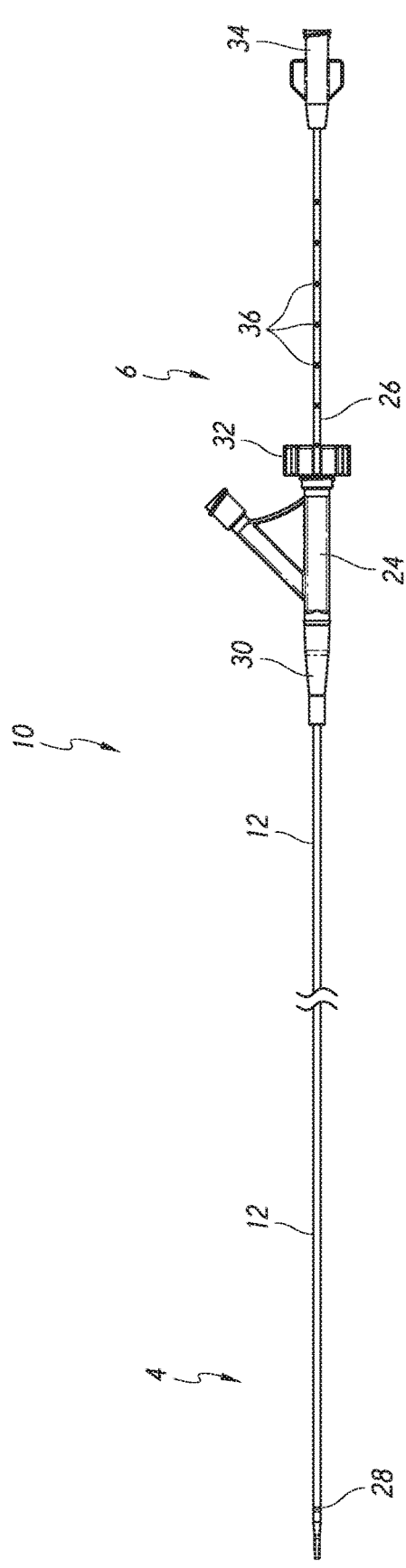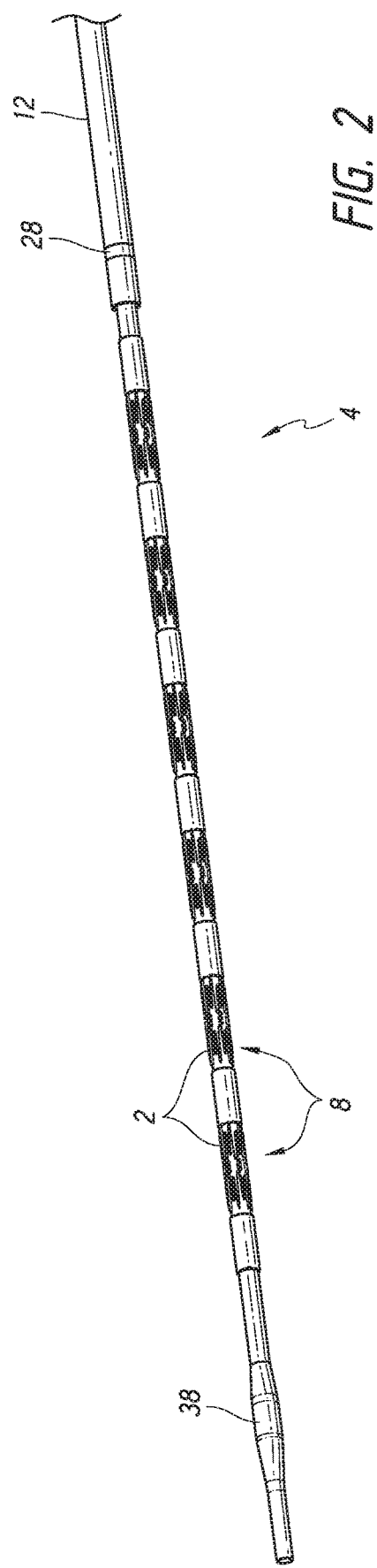

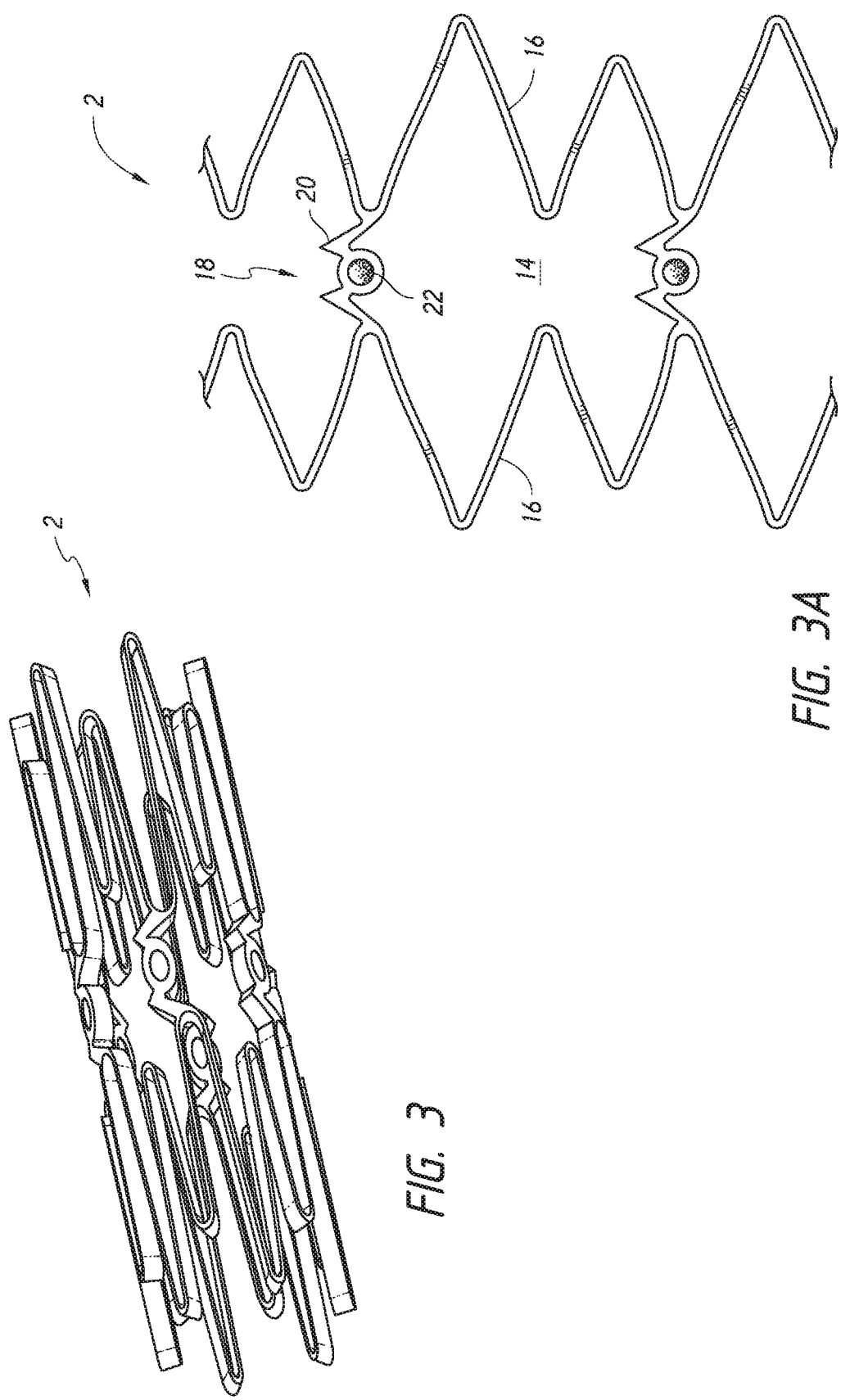

DELIVERY DEVICE AND METHOD OF DELIVERY

INCORPORATION BY REFERENCE TO ANY PRIORITY APPLICATIONS

This application is a continuation of U.S. patent application Ser. No. 14/935,154, filed on Nov. 6, 2015, which is a continuation of U.S. patent application Ser. No. 14/656,462, filed Mar. 12, 2015, which claims the benefit of priority of U.S. Provisional Appl. No. 62/109,534, filed Jan. 29, 2015. All of the above applications are incorporated by reference herein and are to be considered a part of this specification. Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Disclosed herein are delivery devices and methods of delivery. Certain embodiments are described with reference to sequential delivery of multiple intraluminal devices from a delivery device. The delivery devices and methods can be used in procedures to treat atherosclerotic occlusive disease, though they are not limited to these procedures.

Description of the Related Art

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms a hard layer along the wall of an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY OF THE INVENTION

Currently available stents and stent delivery systems have many limitations and drawbacks. There exists a continuing need for improvement in intraluminal devices and associated delivery devices.

According to certain embodiments, a delivery device can be provided for sequential delivery of a plurality of intraluminal devices (e.g. stents, tacks, staples, etc.) held in a compressed state on the delivery device. For purposes of this disclosure the word tack will be used to describe one of many intraluminal devices which can be deployed from a delivery device. The delivery device can comprise a plurality of delivery platforms, each delivery platform configured for holding a tack in a compressed position on the delivery device and having a unique shape, such as a non-constant outer diameter, an hourglass shape, a tapered proximal half, ridges, dimples, etc. This unique shape can be positioned between annular pusher bands that may also be radiopaque markers.

In some embodiments, the unique shape is provided by a sleeve of flexible material with the unique shape surrounding a harder inner shaft. Further, the annular pusher bands can be made of wire or sections of material to increase flexibility while remaining radiopacity.

A tack deployment method can include alignment of radiopaque markers on the outer sheath and the tack to be deployed prior to deployment.

A method of marker band alignment and intraluminal device or tack delivery can be performed. The method can include: advancing a delivery device with a plurality of tacks in a compressed state to a treatment area; each tack comprising a plurality of struts and a radiopaque marker positioned in a central region of the tack, each tack being a same size with the radiopaque marker positioned in a same location; the delivery device comprising an inner core having a plurality of delivery platforms, each delivery platform having one of the plurality of tacks, and an outer sheath covering the inner core and the delivery platforms, the outer sheath having a radiopaque marker band positioned proximally from a distal end; withdrawing the outer sheath until the radiopaque marker band on the outer sheath and radiopaque marker on a first tack to be delivered are aligned; aligning these two radiopaque markers with a treatment area such as a tissue dissection or lesion to be treated before release of the tack; then withdrawing the outer sheath to release the tack.

In some embodiments, a delivery device can comprise an inner shaft, a delivery platform and an outer sheath. The delivery platform can include a pair of annular bands around the inner shaft, both of the annular bands having a first outer diameter and a sleeve. The sleeve can be secured to the inner shaft and positioned between the annular bands. The sleeve can have a lower durometer than the inner shaft and optimally also lower than the pair of annular bands. The sleeve can further have a non-constant outer diameter being less than the first outer diameter of the annular bands. The delivery platform can be configured to receive an intraluminal device for deployment from the delivery device into a vessel and to receive the intraluminal device between the annular bands and on the sleeve. The outer sheath can be positioned on and slidable over the inner shaft and the delivery platform, the outer sheath having a pre-deployment position covering the delivery platform and at least one delivery position where the outer sheath is withdrawn exposing at least one of the annular bands and the sleeve of the delivery platform.

According to some embodiments, a plurality of additional delivery platforms can be included for sequential delivery of a plurality of intraluminal devices. Each additional delivery platform can comprise an additional sleeve and an additional annular band. Each of the annular bands can have a radius on a proximal end and/or comprise a radiopaque helical coil. The radiopaque helical coil can be encased in a polymer having a higher durometer than a polymer that forms the sleeve.

The sleeve can include any number of different shapes and sizes, and can include ridges, dots, dimples, etc.

In some embodiments, a delivery device can comprise an inner shaft, the inner shaft having a nose cone on the distal tip; a delivery platform; and an outer sheath. The delivery platform can comprise a pair of annular bands secured to the inner shaft, both of the annular bands having a first outer diameter; and a sleeve secured to the inner shaft and positioned between the annular bands. The sleeve can have a lower durometer than the inner shaft and optionally also the pair of annular bands. The sleeve may further have a first constant outer diameter section and a second constant outer diameter section having a larger outer diameter than the first, but less than the first outer diameter of the annular bands, and the second constant outer diameter section having a shorter axial length than the first constant outer diameter section, the sleeve further having a smooth tapered transition between the first and second constant outer diameter sections. The delivery platform can be configured to receive an intraluminal device for deployment from the delivery device into a vessel and configured to receive the intraluminal device between the annular bands and on the sleeve. The outer sheath can be positioned on and slidable over the inner shaft and the delivery platform. The outer sheath can have a pre-deployment position covering the delivery platform and at least one delivery position where the outer sheath is withdrawn exposing at least one of the annular bands and the sleeve of the delivery platform.

An intraluminal device deployment method can include one or more of the following steps. Advancing a delivery device with a plurality of intraluminal devices in a compressed state to a treatment area. Each of the plurality of intraluminal devices can comprise a plurality of struts and a radiopaque marker positioned in a central region of the intraluminal device. Each of the plurality of intraluminal devices can be a same size with the radiopaque marker positioned in a same location. The delivery device can comprise an inner shaft having a plurality of delivery platforms, each intraluminal device of the plurality of intraluminal devices positioned at a respective delivery platform of the plurality of delivery platforms, and an outer sheath covering the inner shaft and the plurality of delivery platforms, the outer sheath having a radiopaque marker band positioned proximally from a distal end of the outer sheath. Withdrawing the outer sheath until the radiopaque marker band on the outer sheath and radiopaque marker on a first intraluminal device to be delivered of the plurality of intraluminal devices are aligned. Aligning the aligned radiopaque marker band and the radiopaque marker with the treatment area before release of the first intraluminal device. Withdrawing the outer sheath to release the first intraluminal device. Withdrawing the outer sheath until the radiopaque marker band on the outer sheath and radiopaque marker on a second intraluminal device to be delivered of the plurality of intraluminal devices are aligned.

In some embodiments of the method, aligning the aligned radiopaque marker band and the radiopaque marker with the treatment area can comprise centering the aligned radiopaque marker band and the radiopaque marker at a tissue dissection before release of the first intraluminal device. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until a distal-most end of the outer sheath and a distal-most end of the first intraluminal device are aligned. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band is positioned at a middle of the first intraluminal device. In some embodiments of the method, the first intraluminal device can have a single column of radiopaque markers and withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band encircles the single column of radiopaque markers.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 1 is a side view of a delivery device that has been shortened to facilitate illustration.

FIG. 2 shows a view of the distal end of the delivery device with an outer sheath withdrawn.

FIG. 3 shows an embodiment of intraluminal device or tack.

FIG. 3A shows a flattened section of the tack of FIG. 3.

DETAILED DESCRIPTION OF THE PREFERRED EMBODIMENT

Figure 4:
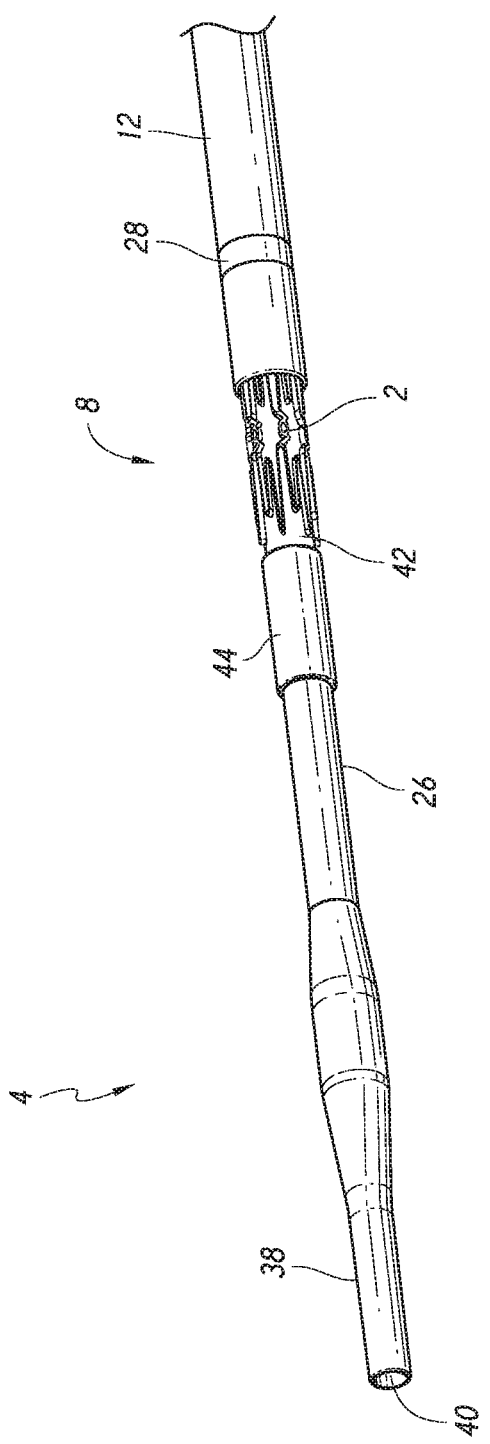
FIG. 4 illustrates a detail view of the distal end of the delivery device with the outer sheath partially withdrawn.

A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow. It will be understood that though the delivery devices and methods described herein are described primarily with reference to vascular procedures, they can also be used in treatments for other parts of the body.

FIGS. 1 and 2 illustrate an embodiment of delivery device 10 that can be used for sequential delivery of multiple intraluminal devices 2. The delivery device 10 can be used in procedures to treat atherosclerotic occlusive disease, though it is not limited to these procedures.

The delivery device 10 of FIG. 1, which has been shortened to facilitate illustration, highlights the distal 4 and proximal ends 6. The proximal end 6 can be held by a physician or other medical professional during a medical procedure. It is used to control delivery of one or more intraluminal devices or tacks 2. FIG. 2 shows the distal end 4 with six (6) intraluminal devices 2, each positioned at a dedicated delivery platform 8. Comparing FIGS. 1 and 2, it can be seen that an outer sheath 12 has been withdrawn from the distal end in FIG. 2. This reveals the delivery platforms 8 and the respective intraluminal devices 2. The intraluminal devices 2 are preferably self-expandable and are shown in their compressed position to represent how they would fit in the delivery platforms. In typical use, the outer sheath 12 would be covering the intraluminal devices 2 when in this position. As will be discussed in more detail below, the outer sheath 12 can be withdrawn in a systematic manner to deploy one intraluminal device 2 at a time at a desired treatment location.

Relatively small intraluminal devices 2, for example with only one (FIGS. 3 & 3A) or two columns of cells, can be delivered at precise treatment locations and space appropriately to not overlap. FIG. 3A shows a flattened section of the tack of FIG. 3. It can be seen that a single column of cells 14 are formed by two concentric rings of undulating struts 16 connected by bridge members 18. The bridge members 18 have a pair of anchors 20 and a radiopaque marker 22. Multiple small intraluminal devices 2 can be used to treat a single or multiple lesions. This can minimize the amount of foreign material in the body, while providing needed holding forces. Various embodiments of intraluminal devices and delivery devices are described in more detail in applicants' related patent application Ser. No. 13/179,458 filed Jul. 8, 2011, published as US 2012/0035705 (IVAS.002P4) and patent application Ser. No. 13/749,643 filed Jan. 24, 2013, published as US 2013/0144375 (IVAS.002P6), both of which are incorporated by reference herein and made a part of this specification.

It will be understood, that the delivery devices and methods can also be used for other intraluminal devices 2, including larger devices, and are not limited to use with intraluminal devices 2 having only one or two columns of cells.

Returning now to FIG. 1, the proximal end 6 of the illustrated embodiment will now be described. The delivery device 10 can include an outer sheath 12, a proximal housing 24, and an inner shaft 26. The outer sheath 12 can be constructed as a laminate of polymer extrusions and braided wires embedded in the polymer extrusions. Flexibility and stiffness can be controlled through the number of braid wires, the braid pattern and pitch of the braid. In other embodiments, the outer sheath can be formed of a hypotube, such as a metal or plastic hypotube. Flexibility and stiffness of the sheath can be controlled by many features such as the slope and frequency of a spiral cut along the length of the hypotube. The outer sheath may also include a radiopaque (RO) marker 28 at or near the distal end. In some embodiments, the radiopaque marker 28 can be an annular band spaced from the distal-most end.

As shown, the outer sheath 12 is a braided shaft and the proximal housing 24 is a bifurcation luer that connects to the outer sheath through a strain relief 30. The strain relief 30 can take any form, such as being made of polyolefin or other similar material.

The bifurcation luer 24 has a main arm to receive the inner shaft 26 and a side arm. The bifurcation luer can be disposed at the proximal end of the outer sheath. The side arm includes a flushing port that is used to flush out air and increase lubricity in the space between the sheath and the inner shaft.

A tuohy borst adapter, hemostatic valve, or other sealing arrangement 32 can be provided proximal of or integrated into the bifurcation luer 24 to receive and seal the proximal end of the space between the inner shaft 26 and the outer sheath 12. The tuohy borst adapter can also provide a locking interface, such as a screw lock, to secure the relationship between the outer sheath and the inner shaft. This can allow the physician to properly place the distal end without prematurely deploying a tack.

The inner shaft is shown with a proximal luer hub 34 and deployment reference marks 36. The deployment reference marks 36 can correspond with the delivery platforms 8, such that the spacing between each deployment reference mark can be the same as the spacing between features of the delivery platforms. For example, the space between deployment reference marks can be the same as the distance between the centers of the delivery platforms.

In some embodiments, a distal most deployment reference mark, or a mark that is different from the others, such as having a wider band or different color, can indicate a primary or home position. For example a deployment reference mark with a wider band than the others can be aligned with the proximal end of the bifurcation luer 24 or hemostatic valve 32. This can indicate to a physician that the outer sheath is in a position completely covering the inner shaft 26 proximal of the nose cone 38. In some embodiments, this alignment can also translate to alignment of the RO marker 28 on the outer sheath to a RO marker on the distal end of the inner shaft 26.

In some embodiments, one or more of the deployment reference marks 36 can represent the number of tacks that are within the system. Thus, once a tack is released, the deployment reference mark 36 will be covered up and the physician can know that the remaining deployment reference marks correspond with the remaining number of tacks available for use. In such an embodiment, the proximal end of the bifurcation luer 24 or hemostatic valve 32 can be advanced to be centered approximately between two reference marks to indicate deployment.

Looking now to FIG. 4, a detail view of the distal end 4 of the delivery device 10 is shown. Features of the illustrated embodiment include the inner shaft 26 with a distal soft tip 38. The tip 38 can be a tapered nose cone. The nose cone 38 serve as a dilating structure to atraumatically displace tissue and help to guide the delivery device through the vasculature. The tip 38 itself may be radiopaque, or a radiopaque element 27 can be incorporated into or near the tip. A guidewire lumen 40 can be seen that extends through the inner shaft 26 to the proximal luer hub 34 (FIG. 1). The guidewire lumen 40 is configured for receipt and advancement of a guidewire therein.

Parts of a delivery platform 8 are also shown. The delivery platforms 8 are identical in the illustrated embodiment, though other embodiments can have different sizes and constructions between different delivery platforms. A crimped or compressed tack 2 is shown in the delivery platform 8.

Figure 5:
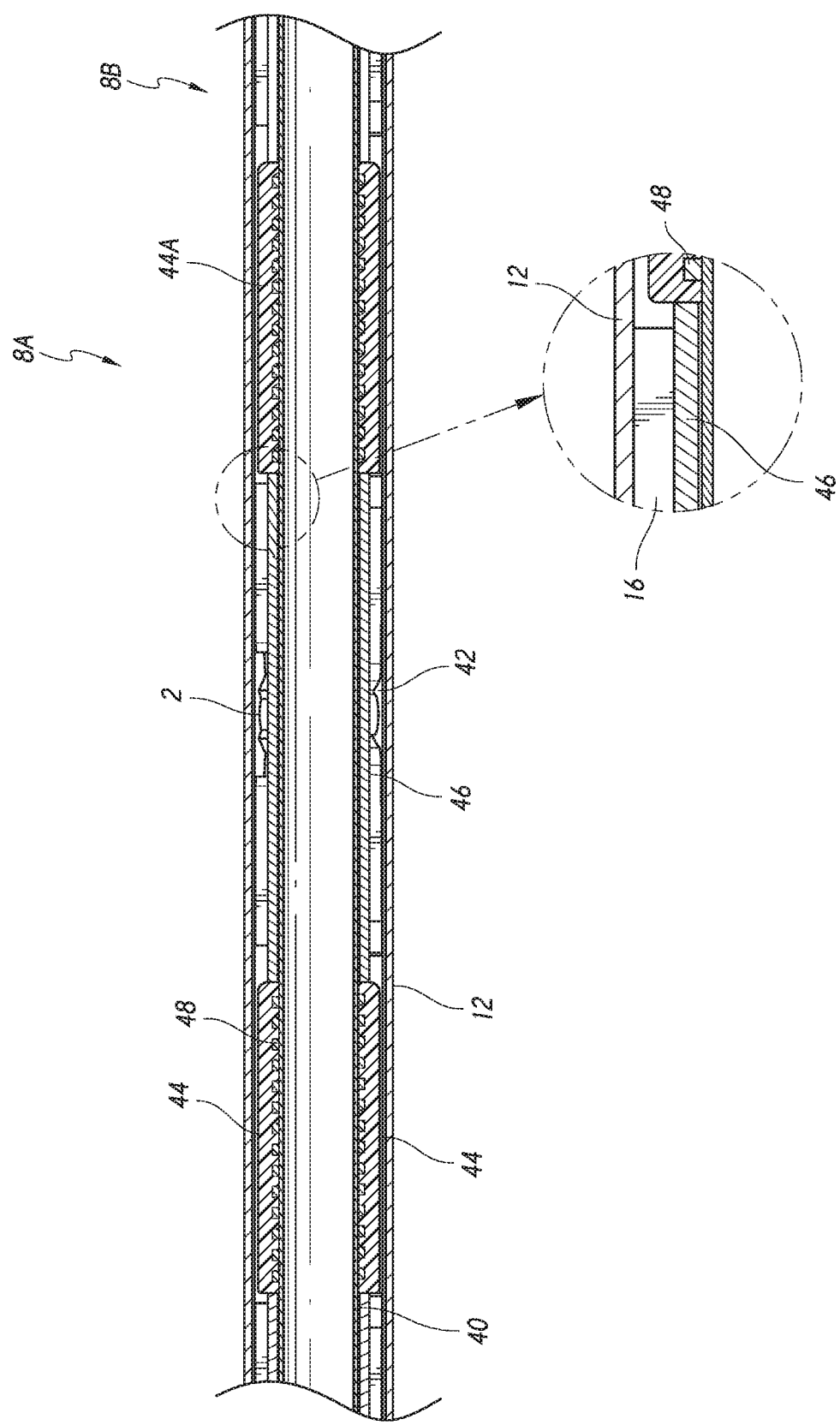
FIG. 5 is a cross section of a delivery device showing an embodiment of delivery platform.

As can be seen in FIGS. 2 and 4, one or more delivery platforms 8 can be disposed on the inner shaft 26 adjacent the distal end 4 of the delivery device 10. Each of the delivery platforms 8 can comprise a recess 42 extending positioned between a pair of annular pusher bands 44. FIG. 5 shows a cross section of a delivery device at one embodiment of delivery platform 8A. In the illustrated embodiment, the proximal annular pusher band 44A of a first platform 8A is also the distal annular pusher band 44A of the platform 8B located immediately proximal (only partially shown). The annular pusher band 44 has a larger outer diameter as compared to the delivery platform at the recess 42. In some embodiments, the recess can be defined as the smaller diameter region next to, or between, one or two annular pusher bands and/or an additional feature on the inner shaft 26.

One or more of the annular pusher bands 44 can be radiopaque marker bands. For example, proximal and distal radiopaque marker bands 44 can be provided to make the ends of the platform 8 visible using standard visualization techniques. The annular marker bands 44 can take any suitable form, for example including one more of tantalum, iridium, and platinum materials. In some embodiments, the pusher bands 44 can be 4 mm long with 6.75 mm recesses between them. A tack of 6.5 mm can be positioned between the pusher bands 44. In some embodiments, the pusher bands can be between 50-70% of the size of the recess and/or the tack. In some embodiments, the pusher bands are about 60%. In other embodiments, the pusher bands can be much smaller, at between 10-20% of the size of the recess and/or the tack. This may be the case especially with longer tacks. In some embodiments, at least the proximal ends of the pusher bands 44 can have a radius to help reduce potential for catching on deployed tacks during retraction of the delivery device.

Reducing the difference in length between the recess and the tack can increase the precision of placement of the tack, especially with tacks having only one or two columns of cells. In some embodiments, the recess can be less than 1, 0.5, 0.4, 0.3, 0.25, or 0.2 mm longer than the tack. The tack can be any number of different sizes, such as 4, 5, 6, 6.5, 8, 10, or 12 mm in length.

The outer sheath 12 can be made of polyether block amide (PEBA), a thermoplastic elastomer (TPE) available under the trade name PEBAX. In some embodiments, the outer sheath 12 can have a thinner inner liner made of a polytetrafluoroethylene (PTFE) such as TEFLON. Any radiopaque marker band(s) 28 or other radiopaque material may be positioned between these two layers. In other embodiments, the radiopaque marker band(s) 28, or other radiopaque material can be embedded within one or more layers of the outer sheath 12. The radiopaque marker band(s) 28 can range from 0.5 mm to 5 mm wide and be located from 0.5 mm to 10 mm proximal from the distal-most tip 52. In some embodiments, the radiopaque marker band(s) 28 can be 1 mm wide and 3 mm proximal from the distal-most tip 52.

In the cross section of FIG. 5 it can be seen that a sleeve 46 is positioned around the inner shaft 26 between the two annular bands 44. In some embodiments, a delivery platform 8 can comprise a sleeve 46 surrounding a shaft 26, where the sleeve 46 is made of a different material, or has different material properties, than the shaft 26. In some embodiments, the sleeve provides a material having a tackiness, a grip, a tread pattern, and/or other features to help the tack stay in place in the delivery platform. In some embodiments, the sleeve can be made of PEBA. The inner shaft according to some embodiments is a composite extrusion made of a PTFE/polyimide composite. The sleeve can be softer than (a lower durometer than) the inner shaft and/or the pusher bands 44. This may be the case even if made of similar types of materials. In some embodiments, the sleeve can be a material having a tackiness, a grip, a tread pattern, and/or other features to help the tack stay in place (e.g. longitudinal position with respect to the inner shaft) while the outer sleeve 12 is withdrawn. This can increase the amount of control during deployment and reduce the likelihood that the tack will shoot out distally from the delivery platform (known in the industry as watermelon seeding). In some cases the outer sheath can be partially removed thereby partially exposing an intraluminal device whereby the intraluminal device can partially expand while being securely retained by the delivery prior to full release.

The sleeve 46 can be sized so that with the tack 2 in the delivery platform 8 there is minimal to no space between the tack and the outer sheath. In some embodiments, the sleeve 46 can be co-molded with or extruded onto the inner shaft 26. In some embodiments, the delivery device 10 can be formed with a single sleeve 46 extending over a length of the inner shaft 26. For example, the sleeve can extend from the first delivery platform to the last delivery platform. The annular bands 44 may surround distinct sections of sleeve 46, or they may be encased by the sleeve 46. In some embodiments, each delivery platform 8 has a separate sleeve 46 positioned in the recess 42. The annular bands 44 may be encased by a different material, or may not be encased at all.

Figure 6A:
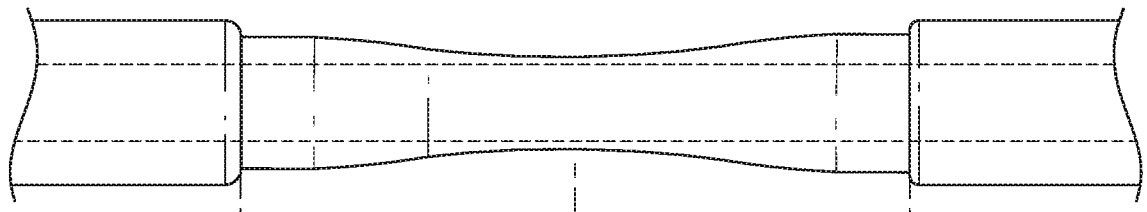
FIGS. 6A-E illustrate various embodiments of delivery platforms having different shapes.
Figure 6B:
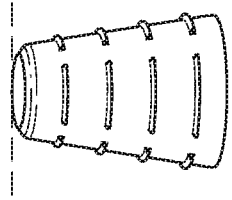
Figure 6C:
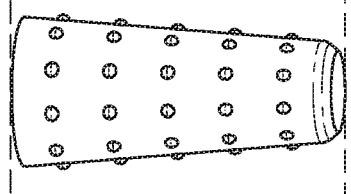
Figure 6D:
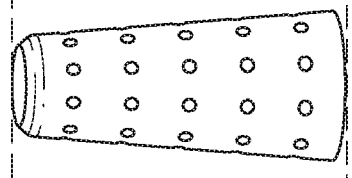

As will be understood from FIG. 5, the sleeve 46 can be cylindrical with a circular cross-section that is maintained across a portion of or the entire length of sleeve. In other embodiments, the sleeve has a unique shape and may include one or more of the following: tapering (FIGS. 6A-E), an hourglass shape (FIG. 6A), ridges (FIG. 6B), dimples (FIG. 6C), dots (FIG. 6D), two or more different diameters (FIG. 6E), etc. Features such as ridges, dots, and dimples can be positioned in in number of different patterns or groupings. In addition, the sleeve (FIGS. 6B-D), or a section of the sleeve (FIG. 6E) can extend along less than the entire recess. In some embodiments, the length of the sleeve or larger outer diameter section can correspond to the length of the tack. For example, the sleeve or larger diameter section can extend ¾, ⅔, ½, ⅖, ⅓, ¼ of the recess and/or tack. Further, the length of the sleeve or larger outer diameter section can be related to the size of struts in the undulating ring 16, such as a proximal most undulating ring. For example, it can extend along the entire, ⅘, ¾, ⅔, or ½ of the length of a strut or the length of the proximal most undulating ring. A short sleeve, or a larger outer diameter section of a sleeve, preferably extends from the proximal end of the recess distally (FIGS. 6D-E), but can also be centered in the recess, positioned on at the distal end (FIG. 6C), or at other positions within the recess.

Figure 6E:
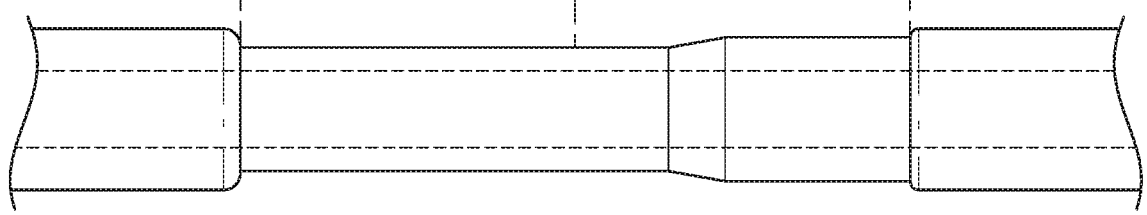

The sleeve of FIG. 6E is shown having two different constant outer diameter sections with a short taper between them. The sleeve can be formed from two separate sections that are thermally bonded together. The tapered portion can also be created by thermal bonding so that there is a smooth transition between the two constant outer diameter sections. As has been mentioned, the larger constant outer diameter section preferably extends from the proximal end of the recess distally. This larger outer diameter section that may or may not have a constant outer diameter can extend along less than the entire recess as has been discussed above.

In some embodiments, an inner shaft 26 can have a lower durometer sleeve 46 between pushers 44. A tack 2 can be crimped onto the sleeve 46 and an outer sheath 12 can constrain the crimped tack in place. The clearance between the sleeve 46 and the outer sheath 12 can result in a slight interference fit between the crimped tack 2 and the inner and outer elements. This slight interference allows the delivery system to constrain the crimped tack during deployment until it is almost completely unsheathed allowing the distal portion of the tack to "flower petal" open and engage the vessel wall, reducing the potential for jumping.

According to some embodiments, the inner shaft 26 can be made of a polyimide-PEBA combination and the lower durometer PEBA sleeve 46 can be thermally bonded in between pushers 44. A tack 2 can be crimped onto the sleeve 46 and a PTFE lined outer sheath 12 can constrain the crimped tack in place.

Returning to FIG. 5, a feature of certain embodiments of radiopaque marker band 44 is shown. As has been mentioned, the sleeve 46 may encase the annular bands 44. Alternatively, another material can encase the metallic bands to form the annular marker bands 44. The annular marker bands 44 can be made of wire 48 or multiple pieces of material or having slits to increase flexibility while remaining radiopacity. In some embodiments the wire can form a helical coil that is wrapped around the inner shaft 26.

Moving now to FIGS. 7A-C, certain methods of deployment will now be described. A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow.

The tacks are preferably self-expandable. Thus, withdrawing the sheath 12 to reveal a tack 2 allows the tack to deploy from the delivery device 10 by self-expansion. The sheath can be withdrawn in small increments to sequentially deliver tacks at desired locations in a blood vessel. In some embodiments, the small increments can correspond with the deployment reference marks 36. The deployment reference marks 36 can be spaced apart at least the length of the tack, so that each tack can be deployed at once, rather than the gradual release typical of a longer stent. This can allow for more precise placement of the tack.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. In some instances the balloon is coated with, or otherwise configured to deliver, a drug or biologic to the tissue. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty can form a dissection. More generally, a dissection occurs when a portion of the plaque or tissue is lifted away from the artery, is not fully adherent to the artery and may be mobile or loose. The plaque or tissue that has been disrupted by dissection protrudes into the flow stream. If the plaque or tissue lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is beneficial to place a metal retaining structure, such as a stent or other intraluminal device to hold open the artery after angioplasty and/or force the dissected material back against the wall of the blood vessel to create an adequate lumen for blood flow.

A variety of delivery methodologies and devices can be used to deploy an intraluminal device, such as a tack 2, some of which are described below. For example, a tack can be delivered into the blood vessel with an endovascular insertion. The delivery devices for the different embodiments of plaque tacks can be different or the same and can have features specifically designed to deliver the specific tack. The tack and installation procedure may be designed in a number of ways that share a common methodology of utilizing an expansion force of the delivery mechanism (such as balloon expansion) and/or the expansion force of an undulating ring to enable the tack to be moved into position in the blood vessel, then released to an expanded state within the blood vessel. A tack deployment method can include alignment of radiopaque markers on the outer sheath and the tack to be deployed prior to deployment.

Figure 7A:
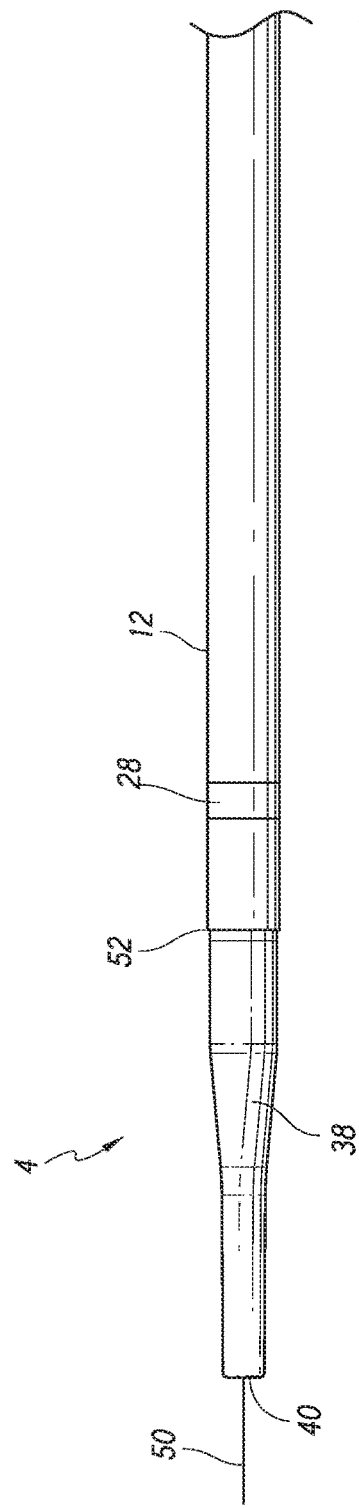
FIGS. 7A-C illustrate certain steps of a deployment method.

Referring now FIG. 7A, a delivery device 10 with an outer sheath 12 is shown in a first pre-deployment state. Multiple tacks 2 can be held by the outer sheath 12 in a compressed state within the delivery device 10. In some embodiments, the tacks 2 are flash frozen in their compressed state to facilitate loading onto the delivery device. The tacks can extend over a given length of the delivery device as has been described.

The delivery device can be advanced over a guidewire 50 in a patient's vasculature to a treatment site. The guidewire 50 can be the same guidewire used in a prior step of a procedure, such as the guidewire used to position an angioplasty balloon. Once positioned at the treatment location, the outer sheath 12 can be withdrawn or retracted to second pre-deployment position (FIG. 7B). The second pre-deployment position can be used to adjust the position of the outer sheath to account for any stretching, tortuosity, etc. that may require some adjustment before releasing a tack. In the second pre-deployment position, the distal end 52 of the outer sheath can be positioned at, or slightly distal of the distal end of a tack to be deployed.

According to some embodiments, the outer sheath 12 can have a radiopaque annular marker band 28 and the tack can also have one or more radiopaque markers 22. The radiopaque markers 22 can be positioned in a column around the tack. The distance "L" from the distal end of the tack to the radiopaque marker 22 can be the same as the distance from the distal end 52 of the outer sheath 12 to the radiopaque annular marker band 28. In some embodiments, this distance is to the center of the markers 22 and marker band 28. In some embodiments, the length "L" on the outer sheath is at least as long as the length "L" on the tack, if not slightly longer. The outer sheath can be free from other radiopaque markers. In addition, the tack can also be free from other radiopaque markers or columns of radiopaque markers. Thus, the outer sheath can have only a single marker band 28 at the distal end that is spaced from the distal-most end 52 of the outer sheath 12 by at least a distance from the distal-most end of the tack 2 to a radiopaque marker 22 or column of radiopaque markers. In the illustrated embodiment, the radiopaque marker 22 or column of radiopaque markers are positioned in the middle of the device. The radiopaque markers are also positioned on bridge members 18 that connect adjacent rings of undulating struts 16. In some embodiments, the radiopaque marker 22 or column of radiopaque markers can be spaced from the distal-most end of the tack by at least one ring of undulating struts 16. In the illustrated embodiment, the radiopaque marker 22 or column of radiopaque markers is not at the distal-most end of the tack 2, but is spaced therefrom.

Having corresponding radiopaque markers 22, 28 on the tack and the outer sheath can allow the physician to align the markers 22, 28 prior to deployment of the tack. Further, the physician can align the aligned markers with the desired area to be treated. As will be understood, all of this alignment can be done using standard visualization techniques. As has been mentioned, the annular pusher bands 44 on the inner shaft can also be radiopaque. In some embodiments, the pusher bands 44 can be identical and can appear different under visualization than both the marker on the outer sheath and the marker on the tack. Thus, it can be clear to the physician where all of the markers are and which is which. For example, the pusher bands 44 can be axially longer than the marker 28 on the outer sheath and the marker on the tack. Further, the markers on the delivery device can be bands, while the marker(s) on the tack can be dots.

Figure 7B:
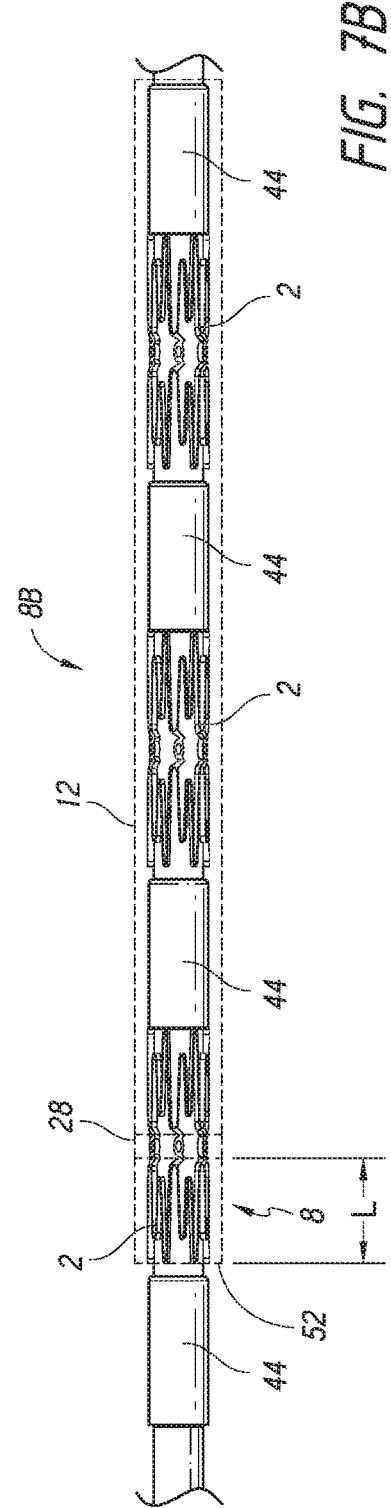

Looking to FIG. 7B, it can be seen that the marker 28 on the outer sheath 12 and the markers 22 on the first tack 2 are aligned and that the distal end of the sheath is positioned at the distal end of the first tack. The delivery device can now be positioned with respect to the lesion for treatment, such as by centering the radiopaque markers at desired location. The sheath can then be withdrawn to place the tack in the desired location.

In some embodiments, the delivery device can have a marker band on the outer sheath positioned proximally from the distal end-one at least half the length of the tack, the tack having a single column of markers at the middle of the device. A method of deployment can include withdrawing the outer sheath until the marker on the outer sheath and the tack to be delivered are aligned, and then aligning these two markers with the middle of the lesion to be treated (or other treatment area) before release of the tack, the release being affected by further withdrawing the outer sheath. It will be understood that markers on the pusher bands 44 can also be used to help align the delivery device before deployment.

Figure 7C:
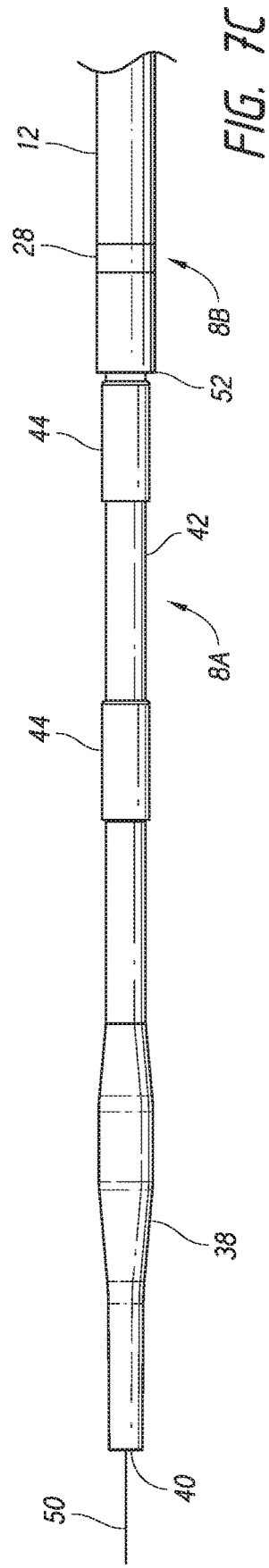

The method can be repeated to deliver multiple tacks (see FIG. 7C with tack shown in the compressed state for reference only). In between tack deployment, the delivery device may be moved to a completely different lesion or treatment area, or simply repositioned to ensure space between adjacent tacks once placed.

As discussed previously, in some embodiments, simultaneous placement of the entire tack can result upon release of the tack from the delivery device. Further, multiple tacks can placed as desired in a distal to proximal placement within the treatment segment of the vessel.

In some embodiments an expandable tack, such as that shown in FIGS. 3 & 3A, can exert a relatively constant force to a wide range of vessel lumen diameters, thereby allowing a single delivery catheter to deploy multiple tacks to varying sized vessels. Ideally the tack can be designed to treat vessels ranging in size from 2 to 8 mm, although other sized tacks could be delivered. It is desirable that the force applied by the tack to the vessel varies 5N or less over a 3 mm expansion range. More ideally the force applied will vary 1.5N or less over a 3 mm expansion range.

There are instances where drug coated balloons are being used as an alternative to placing a stent in the vessel. The balloon can dilate narrowing in the vessel and the drug helps to minimize post inflation inflammatory response which can lead to a re-narrowing of the artery. There is clinical evidence that the combination of a balloon and drug can provide an alternative to the implantation of a typical stent which have been historically used to provide both short term and long term scaffolding. Drug coated balloons are desirable in that there is no long term implant placed in the vessel. There are instances however when the expansion of a drug coated balloon may cause damage to the vessel in the form of a tissue dissection in which case a flap or piece of tissue extends into the lumen of the vessel. The dissection can occur within the balloon treatment zone as well as outside of or adjacent to the treatment zone. In these instances it is helpful to tack the dissected tissue against the arterial wall.

A tack having a low outward force can beneficially be used to treat the dissection where a stent may not be appropriate, or desirable.

In some embodiments, the precise placement of the tack can be set upon positioning of the catheter within the vessel based on the position of a marker. Once positioned, one or more tacks can then be deployed while maintaining the catheter in place and slowly removing the outer sheath.

In some embodiments, one or more tacks can be deployed at a dissection of tissue. When an angioplasty procedure is performed there are typically one of three outcomes: 1) an optimal outcome, no further stenting or over treatment needs to be performed, 2) residual stenosis, usually requiring the placement of a stent to prop open or scaffold the vessel so that it remains open and does not return to the prior occluded or partially occluded state, and 3) a tissue dissection. A tissue dissection can be where the vessel experiences trauma such as the disruption of an arterial wall resulting in separation of the intimal layer. This may or may not be flow limiting. One or more tacks can beneficially be deployed at such a tissue dissection. Small tacks allow for the treatment of a subset of the portion of the blood vessel treated by the balloon angioplasty procedure thereby providing a treatment therapy with does not require the implantation of long metal stents over the entire angioplasty treatment area. Ideally, one or more tacks could be used to treat 60% or less of the length of vessel in the angioplasty treatment area. Small tacks having a single (illustrated) or double column of cells, have been shown to cause less injury and to have shorter recovery times than commonly available stents in treating tissue dissections.

Upon placement of the tack, an intravascular construct is formed in situ. The in situ placement can be in any suitable vessel, such as in any peripheral artery. The construct need not be limited to just two tacks. In fact, a plurality of at least three intravascular tacks can be provided in an intravascular construct formed in situ. In one embodiment each tack has a length of no more than about 8 mm, e.g., about 6 mm in an uncompressed state. In one configuration, at least one of, e.g., each of, the tacks are spaced apart from an adjacent tack by at least about 4 mm, or between about 4 mm and 8 mm or between about 6 mm and 8 mm. Although certain embodiments have a length of 8 mm or less, other embodiments can be longer, e.g., up to about 12 or 15 mm long. Also, neighboring tacks can be positioned as close as 2 mm apart, particularly in vessels that are less prone to bending or other movements. In some embodiments, a delivery device can be preloaded with six tacks, each about 6.5 mm long, and can be used to treat lesions up to 15 cm in length.

In the various delivery devices described herein, the spacing between implanted tacks can be controlled to maintain a set or a minimum distance between each tack. As can be seen, the delivery devices and/or tacks can include features that help maintain the desired distance between tacks. Maintaining proper inter-tack spacing can help ensure that the tacks are distributed over a desired length without contacting each other or bunching up in a certain region of the treated vessel. This can help to prevent kinking of the vessel in which they are disposed.

While a three tack construct formed in situ may be suitable for certain indications, an intravascular construct having at least 5 intravascular tacks may be advantageous for treating loose plaque, vessel flaps, dissections or other maladies that are significantly more elongated (non-focal). For example, while most dissections are focal (e.g., axially short), a series of dissections may be considered and treated as a more elongated malady.

In some cases, even shorter axial length tacks can be used to treat even more spaced apart locations. For example, a plurality of tacks, each having a length of no more than about 7 mm, can be placed in a vessel to treat a tackable malady. At least some of the tacks can be spaced apart from an adjacent tack by at least about 5 mm. In some cases, it may be preferred to provide gaps between adjacent tacks that can range from about 6 mm to about 10 mm.

Optionally, once the tacks are in place, the angioplasty balloon can be returned to the treatment site and inflated to expand the tacks to the desired state of expansion.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A delivery device comprising:
    an inner shaft;
    at least two raised shoulders fixed to and circumferentially surrounding the inner shaft, the at least two raised shoulders comprising at least one proximal raised shoulder and at least one distal raised shoulder;
    a sleeve surrounding at least a portion of the inner shaft, the sleeve having a non-constant outer diameter comprising a first cylindrical section and a second cylindrical section having an outer diameter larger than the first cylindrical section and smaller than the at least two raised shoulders, the sleeve extending between and contacting at least one of the distal edge of the proximal raised shoulder and the proximal edge of a distal raised shoulder, wherein the sleeve comprises a material different than a material of the inner shaft, wherein a distal edge of the proximal raised shoulder, a proximal edge of a distal raised shoulder, and at least one of the inner shaft and the sleeve form at least one recessed delivery platform surrounding the inner shaft and being configured to accept and hold an intraluminal device;
    an outer sheath positioned on and slidable over the inner shaft, the at least two raised shoulders, and the recessed delivery platform, wherein the outer sheath has a pre-deployment position covering every recessed delivery platform of the at least one recessed delivery platform and a deployment position exposing at least one recessed delivery platform of the at least one recessed delivery platform.

2. The delivery device of claim 1, further comprising at least one additional raised shoulder forming at least one additional recessed delivery platform surrounding the inner shaft and being configured to accept and hold an intraluminal device, wherein each additional recessed delivery platform of the at least one additional recessed delivery platform surrounding the inner shaft comprises an additional sleeve surrounding at least a portion of each additional recessed delivery platform of the at least one additional recessed delivery platform.

3. The delivery device of claim 1, wherein the material of the sleeve has a lower durometer than the material of the inner shaft.

4. The delivery device of claim 1, wherein the sleeve comprises a material having at least one of: a higher tackiness than a material of the inner shaft, a higher grip than a material of the inner shaft, and more surface texture than a material of the inner shaft.

5. The delivery device of claim 1, wherein the sleeve and outer sheath are configured to engage an intraluminal device so that a distal end of the intraluminal device may partially expand when a distal end of the outer sheath covers only a proximal end of the intraluminal device contained within the at least one recessed delivery platform surrounding the inner shaft.

6. The delivery device of claim 1, wherein the sleeve further comprises at least one of ridges, dimples, and dots.

7. The delivery device of claim 1, wherein the sleeve extends between and contacts each of the at least two raised shoulders fixed to and circumferentially surrounding the inner shaft.

8. The delivery device of claim 1, wherein the sleeve extends from only one of the at least two raised shoulders fixed to and circumferentially surrounding the inner shaft.

9. The delivery device of claim 1, wherein the sleeve extends at least one of ¾, ⅔, ½, ⅖, ⅓, and ¼, of a length of the at least one recessed delivery platform surrounding the inner shaft.

10. The delivery device of claim 1, wherein the sleeve has a circular cross-section and at least one of the following axial profiles: a proximally faced-taper, a distally faced taper, an hourglass shape, or at least one step.

11. A delivery device comprising:
    an inner shaft;
    at least one recessed delivery platform comprising a distal raised shoulder and a proximal raised shoulder;
    a sleeve surrounding at least a portion of the at least one recessed delivery platform, the sleeve extending between and contacting at least one of the distal raised shoulder and the proximal raised shoulder, the sleeve having a non-constant outer diameter comprising a first cylindrical section and a second cylindrical section having an outer diameter larger than the first cylindrical section and smaller than both the distal raised shoulder and the proximal raised shoulder;
    an outer sheath positioned on and slidable over the inner shaft and the at least one recessed delivery platform, wherein the outer sheath has a pre-deployment position covering the at least one recessed delivery platform and a deployment position exposing at least one recessed delivery platform of the at least one recessed delivery platform, wherein the outer sheath is configured hold at least one intraluminal device within the at least one recessed delivery platform, between the distal raised shoulder and the proximal raised shoulder, and in contact with at least a portion of the sleeve.

12. The delivery device of claim 11 further comprising at least one additional recessed delivery platform and at least one additional sleeve surrounding at least a portion of the at least one additional recessed delivery platform.

13. The delivery device of claim 11, wherein the sleeve and the outer sheath are configured to engage an intraluminal device so that a distal end of the intraluminal device may partially expand when a distal end of the outer sheath covers only a proximal end of the intraluminal device contained within the at least one recessed delivery platform surrounding the inner shaft.

14. The delivery device of claim 11, wherein the sleeve is configured to provide frictional engagement with an intraluminal device to prevent at least one of distal movement and premature deployment of the intraluminal device as the outer sheath is moved from the pre-deployment position to the deployment position.

15. The delivery device of claim 11, wherein the sleeve is configured to maintain a longitudinal position of an intraluminal device as the outer sheath is slid proximally.

16. The delivery device of claim 11, wherein the sleeve extends from the proximal raised shoulder to the distal raised shoulder.

17. The delivery device of claim 11, wherein the sleeve extends from only one of the proximal raised shoulder, distally, and the distal raised shoulder, proximally.

18. The delivery device of claim 11, wherein the sleeve has a circular cross-section and at least one of the following axial profiles: a proximally faced-taper, a distally faced taper, an hourglass shape, or at least one step.

19. The delivery device of claim 11, wherein the sleeve comprises at least one of ridges, dimples, and dots.

20. A delivery device comprising:
an inner shaft;
at least one delivery platform configured to accept and retain a self-expanding intraluminal device, the at least one delivery platform comprising:
a pair of raised annular bands around the inner shaft; and
a sleeve distinct from and surrounding at least a portion of the inner shaft, the sleeve extending between and contacting the pair of raised annular bands, the sleeve having a non-constant outer diameter comprising a first cylindrical section and a second cylindrical section having an outer diameter greater than the first cylindrical section and less than the pair of raised annular bands;
an outer sheath positioned on and slidable over the inner shaft and the at least one delivery platform, wherein the outer sheath has a pre-deployment position covering every recessed delivery platform of the at least one recessed delivery platform and a deployment position exposing at least one recessed delivery platform of the at least one recessed delivery platform, wherein the sleeve surrounding at least a portion of the inner shaft is configured to prevent at least one of longitudinal movement and premature deployment of a self-expanding intraluminal device as the outer sheath is moved from the pre-deployment position to the deployment position.

21. The delivery device of claim 20, wherein a material of the sleeve comprises at least one of: a lower durometer than a material of the inner shaft, a higher tackiness than a material of the inner shaft, a higher grip than a material of the inner shaft, and more surface texture than a material of the inner shaft.

22. The delivery device of claim 20, wherein the sleeve has a circular cross-section and at least one of the following axial profiles: a proximally faced-taper, a distally faced taper, an hourglass shape, or at least one step.

23. The delivery device of claim 1, wherein the sleeve has a smooth tapered transition between the first cylindrical section and the second cylindrical section.

24. The delivery device of claim 1, wherein each of the raised shoulders comprises a radiopaque helical coil.

25. The delivery device of claim 11, wherein the sleeve has a smooth tapered transition between the first cylindrical section and the second cylindrical constant outer diameter section.

26. The delivery device of claim 20, wherein the sleeve has a smooth tapered transition between the first cylindrical section and the second cylindrical section.

27. The delivery device of claim 20, wherein each of the raised annular bands comprises a radiopaque helical coil.

* * * * *